US008026285B2

(12) United States Patent
Bezwada

(10) Patent No.: US 8,026,285 B2
(45) Date of Patent: Sep. 27, 2011

(54) CONTROL RELEASE OF BIOLOGICALLY ACTIVE COMPOUNDS FROM MULTI-ARMED OLIGOMERS

(75) Inventor: Rao S. Bezwada, Hillsborough, NJ (US)

(73) Assignee: Bezwada Biomedical, LLC, Hillsborough, NJ (US)

(*) Notice: Subject to any disclaimer, the term of this patent is extended or adjusted under 35 U.S.C. 154(b) by 423 days.

(21) Appl. No.: 12/203,761

(22) Filed: Sep. 3, 2008

(65) Prior Publication Data
US 2009/0076174 A1 Mar. 19, 2009

Related U.S. Application Data

(60) Provisional application No. 60/969,787, filed on Sep. 4, 2007.

(51) Int. Cl.
A61K 47/48 (2006.01)
(52) U.S. Cl. ...................... 514/772.3; 424/426
(58) Field of Classification Search .................. None
See application file for complete search history.

(56) References Cited

U.S. PATENT DOCUMENTS

| 3,903,007 A | 9/1975 | Ernst |
| 3,987,797 A | 10/1976 | Stephenson |
| 4,020,100 A | 4/1977 | Evans |
| 4,024,871 A | 5/1977 | Stephenson |
| 4,130,639 A | 12/1978 | Shalaby |
| 4,532,928 A | 8/1985 | Bezwada |
| 4,605,730 A | 8/1986 | Shalaby |
| 4,653,497 A | 3/1987 | Bezwada |
| 4,689,424 A | 8/1987 | Shalaby |
| 4,829,099 A | 5/1989 | Fuller |
| 4,886,870 A | 12/1989 | D'Amore |
| 5,082,925 A | 1/1992 | Shalaby |
| 5,378,540 A | 1/1995 | Olson |
| 5,521,431 A | 5/1996 | Tahara |
| 5,759,830 A | 6/1998 | Vacanti |
| 5,801,033 A | 9/1998 | Hubbell |
| 5,834,274 A | 11/1998 | Hubbell |
| 5,834,513 A | 11/1998 | Ptchelintsev |
| 5,843,743 A | 12/1998 | Hubbell |
| 5,895,150 A | 4/1999 | Watabe |
| 5,932,229 A | 8/1999 | Ptchelintsev |
| 5,951,997 A | 9/1999 | Bezwada |
| 6,045,813 A | 4/2000 | Ferguson |
| 6,083,208 A | 7/2000 | Modak |
| 6,106,505 A | 8/2000 | Modak |
| 6,207,139 B1 | 3/2001 | Lee |
| 6,224,579 B1 | 5/2001 | Modak |
| 6,468,519 B1 | 10/2002 | Uhrich |
| 6,596,657 B1 | 7/2003 | Shalaby |
| 6,689,350 B2 | 2/2004 | Uhrich |
| 6,773,721 B1 | 8/2004 | Wong |
| 6,780,799 B2 | 8/2004 | Shalaby |
| 6,861,068 B2 | 3/2005 | Ng |
| 6,869,615 B2 | 3/2005 | Chen |
| 6,887,974 B2 | 5/2005 | Pathak |
| 6,890,561 B1 | 5/2005 | Blatt |
| 6,955,827 B2 | 10/2005 | Barabolak |
| 2002/0028229 A1 | 3/2002 | Lezdey |
| 2002/0169275 A1 | 11/2002 | Matsuda |
| 2003/0158598 A1 | 8/2003 | Ashton et al. |
| 2003/0216307 A1 | 11/2003 | Kohn |
| 2003/0232091 A1 | 12/2003 | Shefer |
| 2004/0096476 A1 | 5/2004 | Uhrich |
| 2004/0117007 A1 | 6/2004 | Whitbourne |
| 2004/0185250 A1 | 9/2004 | John |
| 2005/0048121 A1 | 3/2005 | East |
| 2005/0074493 A1 | 4/2005 | Mehta |
| 2005/0095300 A1 | 5/2005 | Wynn |
| 2005/0112171 A1 | 5/2005 | Tang |
| 2005/0152958 A1 | 7/2005 | Cordes |
| 2005/0238689 A1 | 10/2005 | Carpenter |
| 2006/0013851 A1 | 1/2006 | Giroux |
| 2006/0091034 A1 | 5/2006 | Scalzo |
| 2006/0172983 A1 | 8/2006 | Bezwada |
| 2006/0188547 A1 | 8/2006 | Bezwada |
| 2007/0251831 A1 | 11/2007 | Kaczur |

FOREIGN PATENT DOCUMENTS

| EP | 0099177 | 1/1984 |
| EP | 1460089 | 9/2004 |
| WO | WO 9638528 | 12/1996 |
| WO | WO 2004/008101 | 1/2004 |
| WO | WO 2006/052790 | 5/2006 |

OTHER PUBLICATIONS

J. Org. Chem, 1959, 24, 523-526.
Gutowska et al, J. Biomater, Res., 29, 811-21 (1995).
Hoffman, J. Controlled Release, 6, 297-305 (1987).
Mikos et al, Biomaterials, 14, 323-329 (1993).
Shugens et al, J. Biomed. Mater. Res., 30, 449-462 (1996).
Bulletin of the Material Research Society, Special Issue on Tissue Engineering (Guest Editor: Joachim Kohn), 21(11), 22-26 (1996).
Remington's Pharmaceutical Sciences, 18th ed., Mack Publishing Company, Eason, PA, 1990, p. 1445.
van Dijk-Wolthuis, W.N.W.; Hoogeboom, J.; van Steenbergen, M.; Tsang, S.; and Hennick, W. "Degradation and Release Behavior of Dextran-Based Hydrogels", Macromolecules, 30; (1997) 4639-4645.
van Dijk-Wolthuis, W.N.E.; Tsang, S.; Kettenes-van den Bosch, J.; and Hennick, W. "A new class of polymerizable dextrans with hydrolysable groups: hydroxyethyl methacrylated dextran with and without oligolactate spacer", Polymer, 38 (25); (1997) 6235-6242.
Kurisawa et al, Macromol. Chem. Phys. 199, 705-709 (1998).
Heller, J.; Helwing, R.F.; Baker, R.W.; and Tuttle, M.E. "Controlled release of water-soluble macromolecules from bioerodible hydrogels" Biomaterials, 4; (1983) 262-266.
Brondsted (Brondsted, H.; and Kopccek, J. "Hydrogels for site-specific oral drug deliver: synthesis and characterization" Biomaterials, 12; (1991) 584-592.
Ulbrich, K.; Subr, V.; Seymour, L.W.; and Duncan, R. "Novel biodegradable hydrogels prepared using the divinylic crosslinking agent N, O-dimethacryloylhydroxylamine 1. Synthesis and characterization of rates of gel degradation, and rate of release of model drugs, in vitro and in vivo" Journal of Controlled Release, 24; (1993) 181-190.

Primary Examiner — Robert A Wax
Assistant Examiner — Danah Al-Awadi
(74) Attorney, Agent, or Firm — Vance Intellectual Property, PC

(57) ABSTRACT

The present invention relates to the discovery of biodegradable multi-armed oligomers wherein the end groups of these oligomers have been functionalized with biologically active molecules. The resultant multi-armed oligomers end-functionalized with biologically active molecules have a controllable degradation profile. The hydrolytic degradation of oligomers of the present invention releases the biologically active compound as such with no change in native chemical structure.

38 Claims, No Drawings

US 8,026,285 B2

CONTROL RELEASE OF BIOLOGICALLY ACTIVE COMPOUNDS FROM MULTI-ARMED OLIGOMERS

CROSS REFERENCE TO RELATED APPLICATIONS

This application claims the benefit of U.S. Application No. 60/969,787, filed Sep. 4, 2007, the entirety of which is incorporated herein by reference.

FIELD OF THE INVENTION

The present invention relates to the discovery of biodegradable multi-armed oligomers wherein the end groups of these oligomers have been functionalized with biologically active molecules. The resultant multi-armed oligomers end-functionalized with biologically active molecules have a controllable degradation profile. The hydrolytic degradation of oligomers of the present invention releases the biologically active compound as such with no change in native chemical structure.

BACKGROUND OF THE INVENTION

Biologically active compounds are well known (e.g., aspirin and capsaicin) and have been beneficially administered to patients in need thereof for more than a century. One problem that has been associated with many biologically active compounds is that they can be difficult to dissolve in water or the human body and can also be very difficult to polymerize. Due to the availability and numerous uses of biologically active compounds, it is desirable to enhance their native value by, for example, providing compounds or combinations of compounds with a specific controlled degradation profile or range enabling controlled release of the biologically active compound over an extended, controllable time range. The present invention is directed to these and other important ends.

SUMMARY OF INVENTION

The present invention relates to biodegradable multi-armed (e.g., 2, 3, 4, 5, or 6 arms) oligomers wherein the end groups of these oligomers have been functionalized with biologically active molecules.

The present invention also provides a method of preparing absorbable oligomer compositions comprising functionalized biologically active compounds and a pharmaceutically acceptable carrier.

The present invention also provides a therapeutic method for treating a disease in a mammal comprising administering to a mammal in need of such therapy, an effective amount of an oligomer of the present invention.

The present invention also provides a method of delivering a biologically active compound to a mammal comprising administering to the mammal a biocompatible and biodegradable oligomer of the present invention, which degrades into the biologically active compound.

The present invention also provides an oligomer for use in medical therapy, as well as the use of an oligomer for the manufacture of a medicament useful for the treatment of a disease in a mammal.

The invention also provides processes of functionalizing biologically active compounds and preparation of biologically active oligomer with controlled degradation profiles.

DETAILED DESCRIPTION OF THE PRESENT INVENTION

The present invention relates to the discovery of biodegradable multi-armed (two armed, three armed, four armed, six armed) oligomers wherein the end groups of these oligomers have been functionalized with biologically active molecules. The resultant multi-armed oligomers end-functionalized with biologically active molecules have a controllable degradation profile. The hydrolytic degradation of oligomers of the present invention releases the biologically active compound as such with no change in native chemical structure.

As used herein, the term "biologically active compound" refers to a naturally occurring, semi-synthetic, or synthetic therapeutic agent that provides a therapeutically desirable effect when administered to a mammal (e.g., human). Biologically active compounds capable of incorporation into polymers of the present invention possess at least two functional groups that can each be incorporated into an ester or amide linkage of a polymer of the present invention, such that, upon hydrolysis of the polymer, the therapeutic agent is obtained. The biologically active compounds useful in the present invention have at least one aryl or heteroaryl ring and at least one hydroxyl (OH), substituted or unsubstituted amino, or carboxylic acid substituent on the aromatic or heteroaromatic ring, or functional derivatives of such substituents, such as esters, amides, methyl ethers, and/or glycosides, or other derivatives that would be apparent to those skilled in the art. Additional examples of the number of aromatic groups present in the phenolic include (a) 1, 2, and 3 and (b) 1 and 2. Additional examples of the number of functional (e.g., hydroxyl) groups present on the phenolic include (a) 1, 2, 3, 4, and 5 and (b) 1 and 2.

The biologically active compounds can also comprise other functional groups (e.g., hydroxyl groups, amine groups, and carboxylic acids) that can be used to modify the properties of the polymer (e.g. for branching, for cross linking, for appending other molecules (e.g. another biologically active compound) to the polymer, for changing the solubility of the polymer, or for effecting the biodistribution of the polymer. Lists of therapeutic agents can be found, for example, in: Physicians' Desk Reference, 61$^{st}$ Ed., 2007, Thomson Healthcare Company; USPN Dictionary of USAN and International Drug Names, 2000, The United States Pharmacopoeia Convention, Inc., Rockville, Md.; and The Merck Index, 14$^{th}$ Ed., 2007, John Wiley & Sons. One skilled in the art can readily select therapeutic agents that possess the necessary functional groups for incorporation into the polymers of the invention from these lists.

Therapeutic agents that may be incorporated into the polymers of the invention include suitably functionalized analgesics or general or local anesthetics, anti-convulsants, anti-diabetic agents, anti-fibrotic agents, anti-infectives, anti-bacterials, anti-fungals, anti-neoplastics, cardioprotective agents, cardiovascular agents, anti-thrombotics, central nervous system stimulants, cholinesterase inhibitors, contraceptives, deodorants, dopamine receptor agonists, erectile dysfunction agents, fertility agents, gastrointestinal agents, gout agents, hormones, immunomodulators, immunosuppressive, migraine agents, non-steroidal anti-inflammatory drugs (NSAIDs), motion sickness agents, muscle relaxants, nucleoside analogs, neurodegenerative agents (e.g., Parkinson's disease), obesity agents, ophthalmic agents, osteoporosis agents, parasympatholytics, parasympathommetics, anti-anesthetics, prostaglandins, psychotherapeutic agents, respiratory agents, sedatives, hypnotics, skin and mucous membrane agents, smoking cessation agents, sympatholytics, urinary tract agents, vaginal agents, and vasodilators, and the like (see Physicians' Desk Reference, 61$^{st}$ Ed., 2007, Thomson Health Care).

Phenol is the simplest example of a phenolic compound, but most phenolics have two or more hydroxyl groups and are in many instances bioactive substances occurring widely in food plants that are eaten regularly by substantial numbers of animals and people. These food-plant bioactive phenolic compounds have typically been found to be safe compounds. Included in the definition of biologically active phenolics are highly substituted poly-phenols whose structures include condensed rings.

Examples of naturally occurring biologically active phenolics include bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, sinapic acid, vanillic acid, vanillin, and derivatives thereof.

Capsaicin is a biologically active phenolic that is the active component of cayenne pepper. The capsaicin is an amide of vanillylamine and $C_8$ to $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4 times daily reportedly may help peripheral neuropathic pain, post-herpetic neuralgia, trigeminal neuralgia, psoriasis and fibromyalgia. It may also be useful for diabetic neuropathy, cluster headaches, earache, osteo- and rheumatoid arthritis. Capsaicin is a powerful pain reliever.

Naproxen, paracetanol, acetaminophen and acetylsalicylic acid are biologically active phenolics that belong to the class of drugs called non-steroidal anti-inflammatory drugs or NSAIDs. It is generally believed that NSAIDs provide relief by blocking the action of prostaglandins, which are hormone-like substances that contribute to pain, inflammation, fever and muscle cramps.

Phenolic moieties, synthetic and naturally occurring, are part of many drugs. Examples of these medicinals include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, buphenoide, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoum-acetate, etilefrine, etiroxate, exalamide, exifone, fendosal, fenoldopam mesilate, fenoterol, fenoxedil, fenticlor, flopropione, floredil, fluorescein, folescutol, formo-terol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochlor-ide, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxo-line, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theo-drenaline, tioclomarol, tioxolone, α-tocopherol (vitamin E), tofisopam, tolcapone, tolterodine, tranilast, tretoquinol, triclosan, trimazosin, trimetazidine, trimethobenz-amide, trimethoprim, trimetozine, trimetrexate glucuronate, troxipide, verapamil, vesnarinone, vetrabutine, viloxazine, warfarin, xamoterol.

Other bioactive phenolics include acacetin, 4-acetamido-2-methyl-1-naphthol, acetaminophen, albuterol, allenolic acid, aloe emodin, aloin, β-amino-4-hydroxy-3,5-di-iodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromo-nar, chrysin, cinametic acid, clorophene, coniferyl alcohol, p-coumaric acid, coumes-trol, coumetarol, daphnetin, datiscetin, deoxyepinephrine, 3,5-diiodothyronine, 3,5-di-iodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophe-none, gallic acid, gardenins, genistein, gentisyl alcohol, gepefrine, geranylhydroqui-none, [6]-gingerol, gossypol, guaiacol, guaifenesin, harmalol, hematoxylin, hinderin, homoeriodictyol, homogentisic acid, homovanillic acid, hydroxyamphetamine, 2-hyd-roxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxy-phenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, tiratricol, tyrosine, vanillic acid, and vanillin.

Examples of biologically active amino compounds include Aceclofenac, Acediasulfone, Alminoprofen, Amisulpride, AmLexanox, Amodiaquine, Amosulalol, Amoxicillin, Amsacrine, Anileridine, Azacyclonol, Baccofen, Balsalazide sodium, Benzocaine, Bromopride, Bumetanide, Carprofen, Carvedilol, Carzenide, Cefprozil, Cinitapride, Clebopride, Clenbuterol, Diclofenac, Ethoxzolamide, Flufenamic acid, Furosemide, lobenzamic acid, locetamic acid, Mefenamic acid, Nadoxolol, D-Nor-pseudoephedrine and paracetamol.

Examples of biologically active carboxylic acid compounds include Acemetacin, Aceclofenac, Acediasulfone, Adipiodone, Alminoprofen, AmLexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, locarmic acid, locetamic acid, Iodoxamic acid, Ioglycamic acid, Iophenoic acid, Iotroxic acid, Mefenamic acid, Naproxen, Nedocromil, Repaglinide, Salazosulfapyridine, Salicylic Acid, Salsalate, and Sarpogrelate.

Flavonoids, sometimes called bioflavonoids, are 3-ring phenolic compounds consisting of a double ring attached by a single bond to a third ring. Examples include flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, and leucoanthocyanins. Flavonoids include the water-soluble pigments, such as anthocyanins, that are found in cell vacuoles. Flavonols are colorless or yellow flavonoids found in leaves and many flowers.

A therapeutic dose of bioflavonoids is helpful for conditions related to Chronic Venous Insufficiency (CVI). Some examples are: thrombophlebitis, thrombosis, varicose veins, leg ulcers, spider veins, hemorrhoids, chronic nosebleeds, prolonged menstrual bleeding. Even eye problems like macular degeneration and diabetic retinopathy have been helped with bioflavonoids. Along with the anti-inflammatory effects, bioflavonoids can be very helpful for tendonitis, arthritis, rheumatoid arthritis, joint injury, fibromyalgia, cellulite, and gout. Bioflavonoids, specifically proanthcyanidins, are found in grape seed extract. The proanthcyanidins appear to enhance the activity of vitiamin C. The bioflavonoids in grape seed extract may also reduce the painful inflammation of swollen joints and prevent the oxidation of cholesterol in arteries that leads to plaque in the arterial walls.

Isoflavones exert a broad spectrum of biological activities. Besides antioxidant and estrogenic activities, isoflavones protect against several chronic diseases. Results of epidemiological studies indicate that consumption of soybean isoflavones lowers the incidence of breast, prostate, urinary tract and colon cancers. They also provide protection against coronary heart diseases and osteoporosis. Examples of isoflavones include are glycitein (isoflavone), daidzein, prunetin, biochanin A, orobol, santal, pratensein, formononetin, genistein, glycitein, and the glucosides, β-glycosides and other derivatives of the aforementioned isoflavones.

Further examples of biologically active compounds with hydroxyl, carboxyl and/or amino groups useful in the present invention may be found in the following texts, which are hereby incorporated in their entireties herein by reference.

a. Shahidi, Ferriodoon and Marian Naczk, *Phenolics in Food and Nutriceuticals*, Boca Raton, Fla.: CRC Press, 2003.
b. Kleemann, A. et al, *Pharmaceutical Substances,* 4th Edition, Thieme (2000).
c. *Phenolic Compounds in Food and Their Effects on Health II; Antioxidants and Cancer Prevention*, ACS Symposium Series No. 507, Washington, D.C.: ACS, 1992.
d. *Food Phytochemicals for Cancer Prevention I*, ACS Symposium Series N. 546, Washington, D.C.: ACS, 1994.
e. *ROMPP Encyclopedia Natural Products*, New York: Thieme, 2000.
f. *The Merck Index,* 14th edition, John Wiley & Sons, 2007.
g. *A Single Source for Flavonoids and Coumarins* (2005-2006), INDOFINE Chemical Company, Inc. 2006.

The present invention provides novel oligomers of formulae I and/or II or a pharmaceutically acceptable salt thereof:

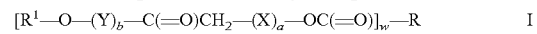

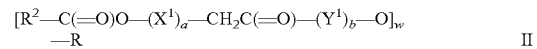

wherein:

$R^1$—O— is a biologically active compound residue;

$R^2$—C(=O)O— is a biologically active compound residue;

X is selected from: —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O) (CH$_2$)$_y$—, or —OC(=O)CH$_2$(OCH$_2$CH$_2$)$_z$—.

$X^1$ is selected from: —CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_z$CH$_2$C(=O)O—;

Y is selected from: —C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$—O—(CH$_2$CH$_2$O)$_n$—;

$Y^1$ is selected from: —OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

R is a di-, tri, tetra-, penta- or hexaradical derived from $C_{2\text{-}25}$ alkyl, aryl, or aryl-$(C_{1\text{-}6}\text{alkyl})_{1\text{-}3}$-, wherein from 1-3 of the CH$_2$ groups within the alkyl chain are optionally independently replaced by O atoms, such that each of said O atom is attached only to carbon atoms in the alkyl chain, with the proviso that multiple O atoms that replace CH$_2$ groups within the alkyl chain must be separated from each other by at least two carbon atoms and from the di-, tri, tetra-, penta- or hexaradical chain ends by at least one carbon atom; or R is the backbone of a polymer or copolymer bearing carboxylic acid and/or hydroxyl functional groups, where the average molecular weight of the polymer or copolymer is between 500 to 5000 and wherein w is an integer from about 6 to about 50;

a is independently selected from 1, 2, 3, 4, 5, 6, 7, 8, 9, and 10;

b is independently selected from 1, 2, 3, 4, 5, 6, 7, 8, 9, and 10;

each a and b is independently an integer from about 1 to about 10;

each m, n, y, and z is independently an integer from about 2 to about 24; and w is an integer from about 2 to about 6.

The groups represented by X, $X^1$, $Y^1$, and $Y^2$ are attached as shown. Their left hand sides are attached to the group shown in the corresponding formula to be on the left of the X, $X^1$, Y, or $Y^1$ group and on their right hand sides to the group shown in the corresponding formula to be on the right of the X, $X^1$, Y, or $Y^1$ group.

In some preferred embodiments of oligomers or pharmaceutically acceptable salts thereof of formula I or II, $X^1$ and $Y^1$ are derived from different hydroxyacid or lactone precursors.

In some preferred embodiments of oligomers or pharmaceutically acceptable salts thereof of formula I or II, X and Y are derived from different hydroxyacid or lactone precursors.

In other preferred embodiments of oligomers or pharmaceutically acceptable salts thereof of formulas I or II, R is a di-, tri-, tetra-, penta- or hexaradical derived from $C_{2-25}$ alkyl, aryl, preferably phenyl, or aryl-$(C_{1-6}$alkyl$)_{1-3}$-, preferably phenyl-$(C_{1-6}$ alkyl$)_{1-3}$-. Whether R is a di-, tri, tetra-, penta- or hexaradical is determined by w. For example, when w is 2, R is a diradical; when w is 4, R is a tetraradical, and so forth. In certain preferred embodiments wherein R is derived from $C_{2-25}$ alkyl or aryl-$(C_{1-6}$ alkyl$)_{1-3}$—, 1-3 of the $CH_2$ groups within the alkyl chain are optionally independently replaced by O or S atoms, preferably by O atoms, such that each of said O or S atoms is attached only to carbon atoms in the alkyl chain, preferably with the proviso that the O or S atoms are separated from the di-, tri, tetra-, penta- or hexaradical chain ends by at least one carbon atom and that multiple O or S atoms in the diradical chain must be separated from each other by at least two carbon atoms. Alternatively in some preferred embodiments, when R is alkyl, it is more preferably $(CH_2)_2$, $(CH_2)_3$, $CH(CH_2)_3$, $C(CH_2)_4$, or $C(CH_2CH_3)(CH_2)_3$. In still other preferred embodiments, R is $(CH_2)_3$, and wherein the C-2 $CH_2$ group within the $(CH_2)_3$ chain is optionally replaced by an O atom. In yet other preferred embodiments, R is $(CH_2)_2$, $(CH_2)_3$, $(CH_2)_4$, $(CH_2OCH_2)$, or $(CH_2CH_2OCH_2CH_2)$. In still other preferred embodiments, R is $(CH_2CHCH_2)$ when w is 3, or $(C(CH_2)_4)$ when w is 4.

In certain other preferred embodiments, the present invention provides novel multi-armed oligomers of formulae I or II or a pharmaceutically acceptable salt thereof, wherein:

R is a di-, tri-, tetra-, penta- or hexaradical derived from a $C_{2-12}$ alkyl, phenyl, and phenyl-$(C_{1-6}$ alkyl$)_{1-3}$-.

As used herein, the term "aryl-$(C_{1-6}$ alkyl$)_{1-3}$-" refers to a aryl ring, preferably a benzene ring, having 1 to 3 pendant alkyl groups, wherein the aryl-$(C_{1-6}$ alkyl$)_{1-3}$-, preferably phenyl-$(C_{1-6}$ alkyl$)_{1-3}$-moiety, is attached to the remainder of the structure in a given formula through its pendant alkyl group(s).

In certain preferred embodiments of the present invention, a is independently an integer from about 1 to about 5. Alternatively preferred, each a is independently an integer from about 1 to about 6, preferably from 1 to about 3, with from 1 to about 2 being even more preferred.

In other preferred embodiments of the present invention, b is independently an integer from about 1 to about 5. Alternatively preferred, each b is independently an integer from about 1 to about 6, preferably from 1 to about 3, with from 1 to about 2 being even more preferred.

In still other preferred embodiments of the present invention, w is the integer 2, 3, or 4.

The present invention also provides novel multi-armed oligomers of formulae I or II or a pharmaceutically acceptable salt thereof, wherein the moiety R and the "w" number of attached oxygen atoms (R—$[O]_w$) is O$(CH_2)_2$O, wherein w is 2; O$(CH_2)_3$O, wherein w is 2; CH$(CH_2O)_3$, wherein w is 3; C$(CH_2O)_4$, wherein w is 4; and C$(CH_2CH_3)(CH_2O)_3$, wherein w is 3.

In other preferred embodiments of the present invention, each X is independently —OC(═O)$CH_2$—, —OC(═O)CH($CH_3$)—, —OC(═O)$CH_2OCH_2CH_2$—, or —OC(═O)$CH_2CH_2CH_2CH_2CH_2$—; more preferably —OC(═O)$CH_2$— or —OC(═O)CH($CH_3$)—.

In certain preferred embodiments of the present invention, each $X^1$ is independently —$CH_2$C(═O)O—, —CH($CH_3$)C(═O)O—, —$CH_2CH_2OCH_2$C(═O)O—, or —$CH_2CH_2CH_2CH_2CH_2$C(═O)O—, more preferably —$CH_2$C(═O)O— or —CH($CH_3$)C(═O)O—.

In some preferred embodiments of the present invention, each Y is independently —C(═O)$CH_2$O—, —C(═O)CH($CH_3$)O—, —C(═O)$CH_2OCH_2CH_2$O—, or —C(═O)$CH_2CH_2CH_2CH_2CH_2$O—; more preferably —C(═O)$CH_2$O— or —C(═O)CH($CH_3$)O—.

In some other preferred embodiments of the present invention, each $Y^1$ is independently —OCH$_2$C(═O)—, —OCH($CH_3$)C(═O)—, —OCH$_2$CH$_2$OCH$_2$C(═O)—, or —OCH$_2$CH$_2$CH$_2$CH$_2$CH$_2$C(═O)—, more preferably —OCH$_2$C(═O)— or —OCH($CH_3$)C(═O)—.

Examples of polymers or copolymers containing carboxylic acid group and/or hydroxyl functional groups include poly(acrylic acid), poly(acrylic acid-co-maleic acid), poly(ethylene glycol), branched poly(ethylene glycol), and poly(acrylic acid-graft-polyethylene glycol).

Examples of biologically active compounds include phenolic compounds including phenols, naphthols, indoles, acetophenones, benzophenones, coumarins, furanocoumarins, alkaloids, catechins, chromones, chalcones, flavonoids or bioflavonoids, isoflavones, drugs containing phenolic groups, and natural products containing phenolic groups.

Examples of biologically active dihydroxy compound that can be used to prepare a polymer of the present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active hydroxy/amino compounds that can be used to prepare a polymer of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, and paracetamol.

Examples of biologically active dicarboxylic acid compounds that can be used to prepare a polymer of the present invention include Adipiodone, Cromoglicic acid, Eprosartan, locarmic acid, Iodoxamic acid, Ioglycamic acid, Iotroxic acid, Nedocromil.

Examples of biologically active hydroxy/carboxylic acid compounds that can be used to prepare a polymer of the present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids useful in the present invention include but not limited to 4-hydroxycinnamic acid, Caffeic acid, Chlorogenic acid, Ferulic acid, Sinapinic acid, Vanillic acid, Acemetacin, Bentiromide, Cinmetacin, Clometacin, Diflunisal, Fendosal, Indometacin, lophenoic acid, Naproxen, Repaglinide, Salazosulfapyridine, Salicylic Acid, Salsalate, and Sarpogrelate.

Examples of biologically active amino/carboxylic acid compounds that can be used to prepare a polymer of the present invention include Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Some structures of Biologically Active Compounds bearing hydroxyl functional groups useful in present invention are shown below.

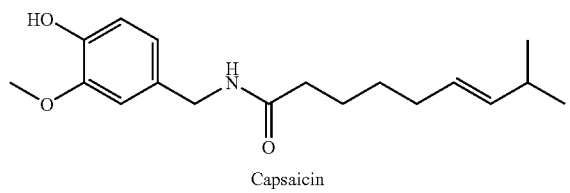
Capsaicin

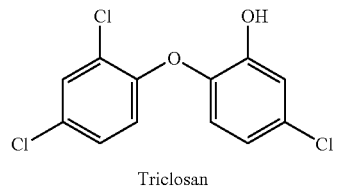
Triclosan

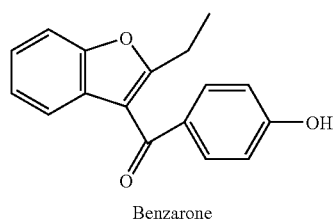
Benzarone

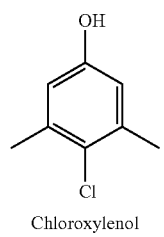
Chloroxylenol

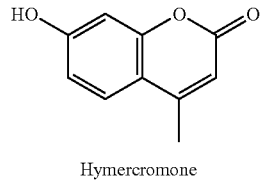
Hymercromone

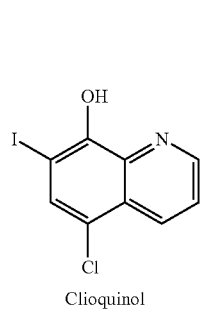
Clioquinol

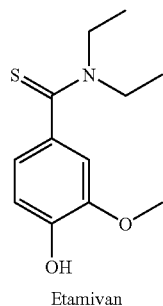
Etamivan

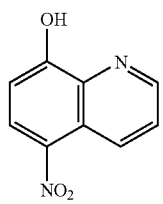
Nitroxoline

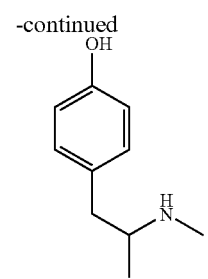
Pholedrine

Oxyquinoline

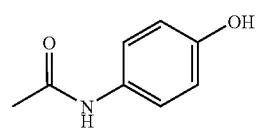
Paracetamol

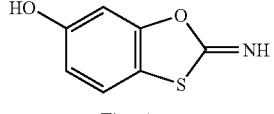
Tioxolone

Examples of Biologically Active Compounds bearing carboxylic acid functional groups include but not limited to Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic cid, Mefenamic acid, Naproxen, Nedocromil, Repaglinide, Salazosulfapyridine, Salicylic Acid, Salsalate, and Sarpogrelate.

Some structures of biologically active compounds bearing carboxyl functional groups useful in present invention are shown below.

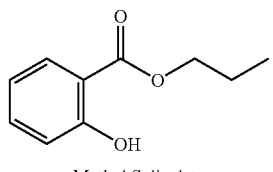
Methyl Salicylate

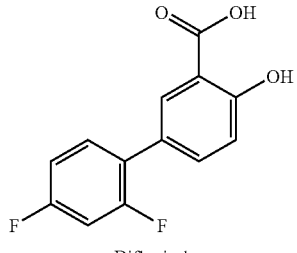
Diflunisal

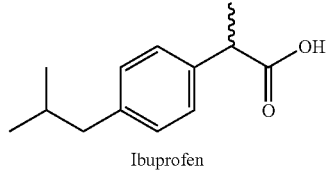
Ibuprofen

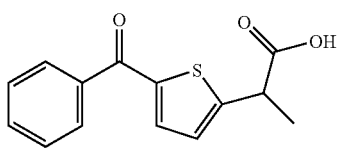
Tiaprofenic Acid
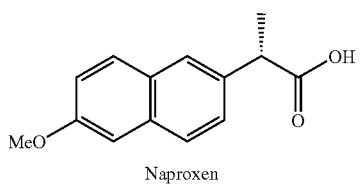
Naproxen
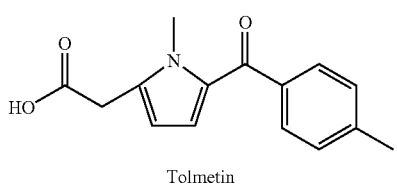
Tolmetin
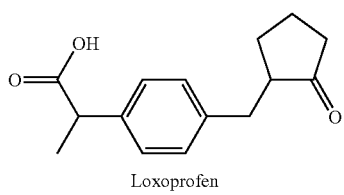
Loxoprofen
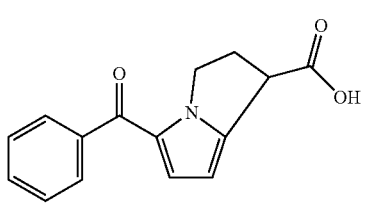
Ketorolac
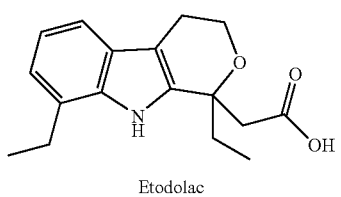
Etodolac
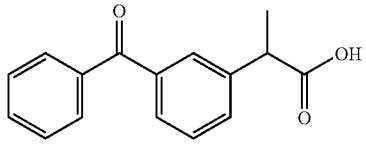
Ketoprofen
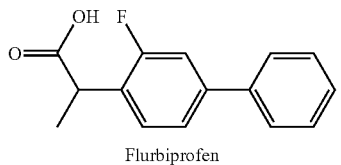
Flurbiprofen
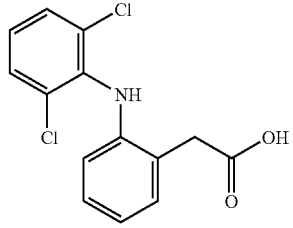
Diclofenac
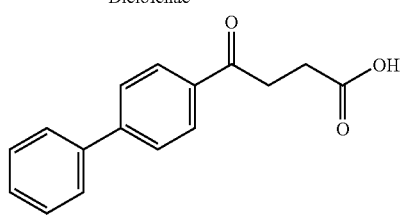
Fenbufen
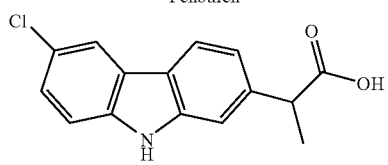
Carprofen
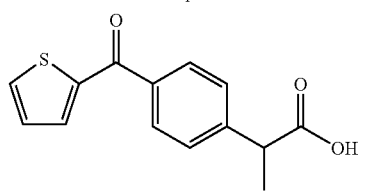
Suprofen
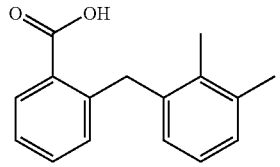
Mefenamic acid
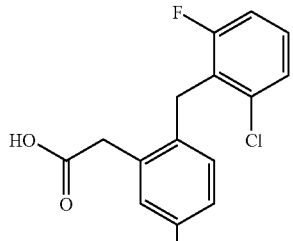
Lumiracoxib
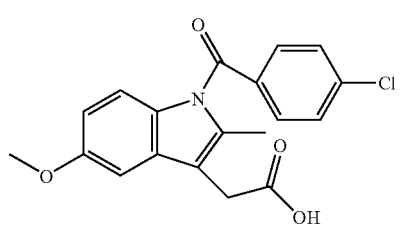
Indometacin Some of the biodegradable oligomers of the present invention can be prepared in two steps as shown in Scheme 1. In the first step, a multi-armed backbone for the oligomers is derived by the functionalization of multi-armed acid molecules (shown as a tetra-acid) with safe and biocompatible monomers or oligomeric segments containing repeat units derived from them to form multi-armed hydrolysable linker of formula A. Similarly, Biologically Active Compounds bearing hydroxyl functional groups can also be functionalized with safe and biocompatible monomers or oligomeric segments containing repeat units derived from them to form functionalized Biologically Active Compounds of Formula B. In the second step, multi-armed hydrolysable linker of formula A and functionalized Biologically Active Compounds of Formula B are reacted together in stoichiometric amounts to form multi-armed, biodegradable end functionalized therapeutic oligomers of Formula I of the present invention with controllable hydrolytic degradation profiles. The resulting multi-armed oligomers of the present invention can provide site specific delivery of bioactive compounds upon biodegradation by hydrolytic and/or enzymatic actions with controlled release of biologically active compounds as such with no change in native chemical structure.

Scheme 2. In the first step, a multi-armed biodegradable backbone can be derived by the functionalization of multi-armed hydroxyl (polyol) molecules with safe and biocompatible monomers or oligomeric segments containing repeat units derived from them to form multi-armed hydrolysable linkers of formula C. Similarly, Biologically Active Compounds bearing carboxyl functional groups can also be functionalized with safe and biocompatible monomers or oligomeric segments containing repeat units derived from them to form functionalized Biologically Active Compounds of Formula D. In the second step, multi-armed hydrolysable linker of formula C and functionalized Biologically Active Compounds of Formula D are reacted together in stoichiometric amounts to form multi-armed, biodegradable end functionalized therapeutic oligomers of Formula II of the present invention with controllable hydrolytic degradation profile. The resulting multi-armed oligomers of the present invention can provide site specific delivery of bioactive compounds upon biodegradation by hydrolytic and/or enzymatic actions with controlled release of biologically active compounds as such with no change in native chemical structure.

Scheme 1

Step 1

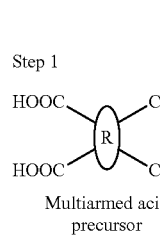
Multiarmed acid precursor

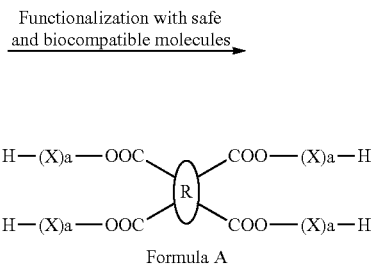
Formula A
Funcionalized multiarmed acid precursor with a = 1 to 6

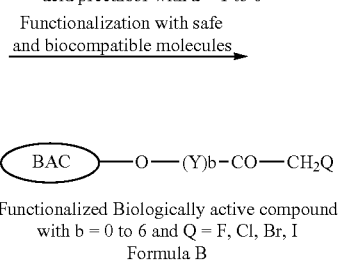
Biologically active compound bearing hydroxyl group

Functionalized Biologically active compound with b = 0 to 6 and Q = F, Cl, Br, I
Formula B Step 2

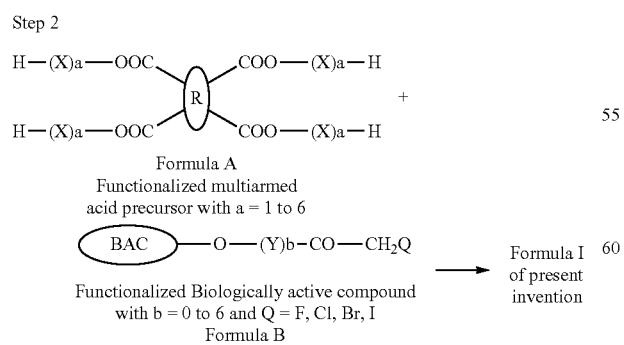
Formula I of present invention

In another embodiment of the present invention, oligomers of present invention can be prepared in two steps as shown in

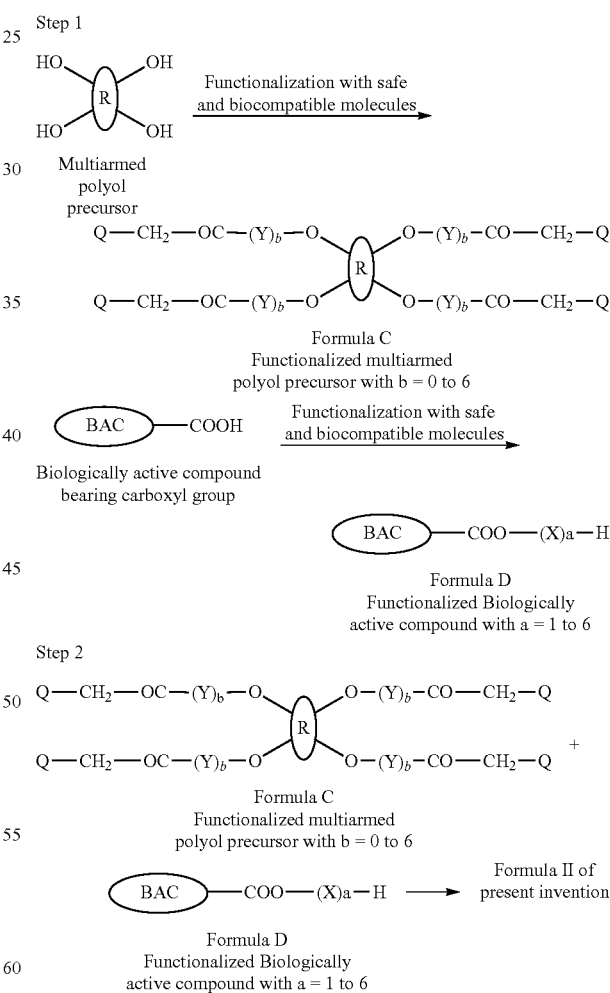

Some examples of linear and multi-armed hydrolysable linker precursors of present invention are shown below: (e.g., $-OC(=O)]_w-R$, wherein each carboxylic acid proton (H) present in the di- or poly acid shown below is absent in the linker):

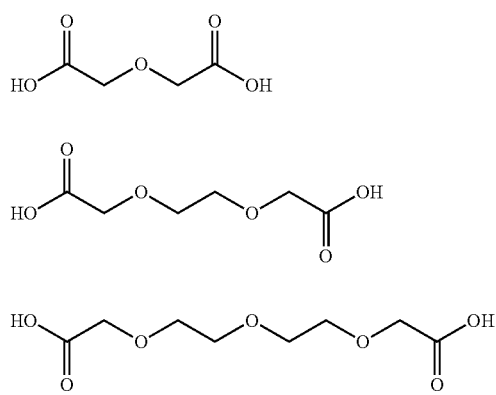
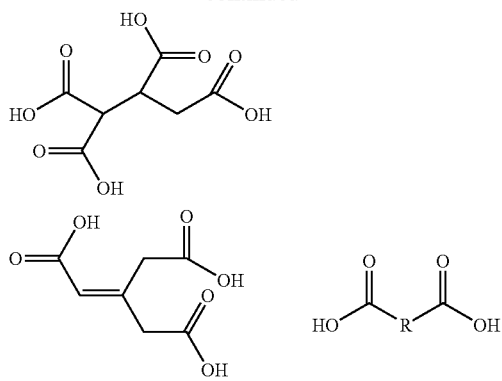

n = 10-50

Examples of the number-average molecular weight of PEG (polyethylene glycol) include 400, 500, 600, 700, 800, 900, to 1000.

Some examples of linear and multi-armed hydrolysable linkers of the present invention are shown below (e.g., $-(X)_a-OC(=O)]_w-R$, wherein each carboxylic acid proton (H) shown is absent in the linker):

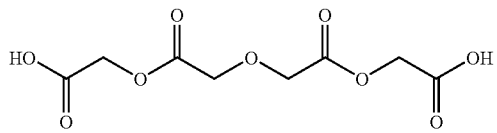

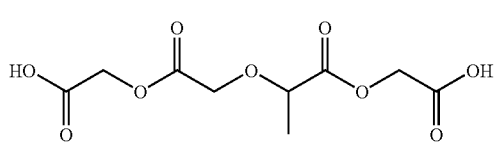

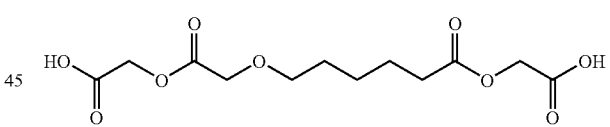

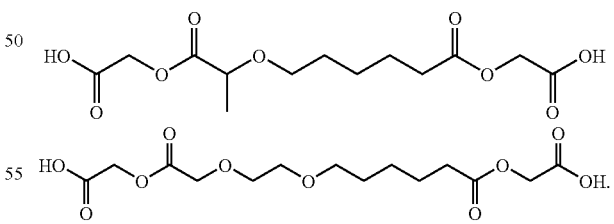

For example, the first diacid derived linker in the list shown directly above has R as a three carbon diradical, wherein one of the $CH_2$ groups in the diradical is replaced by an oxygen atom, X is $-OC(=O)CH_2-$, a is the integer 1, and w is the integer 2.

Some examples of linear and multi-armed hydrolysable precursors and linkers of the present invention are shown below (e.g., $-CH_2C(=O)-(Y^1)_b-O]_w R$):

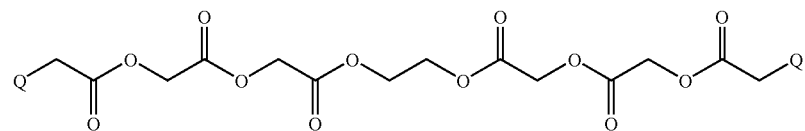
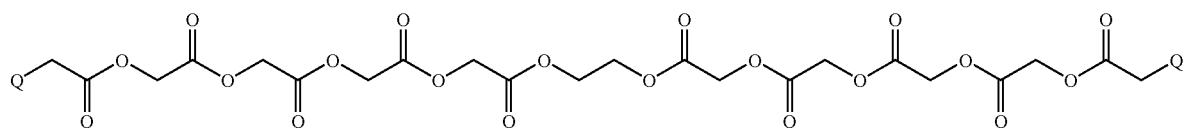
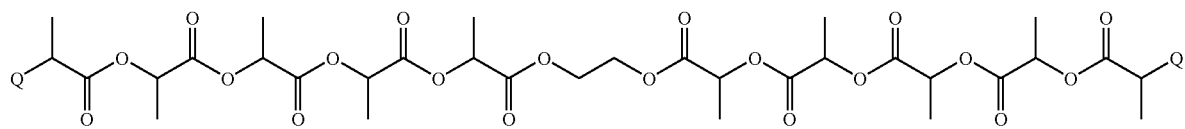
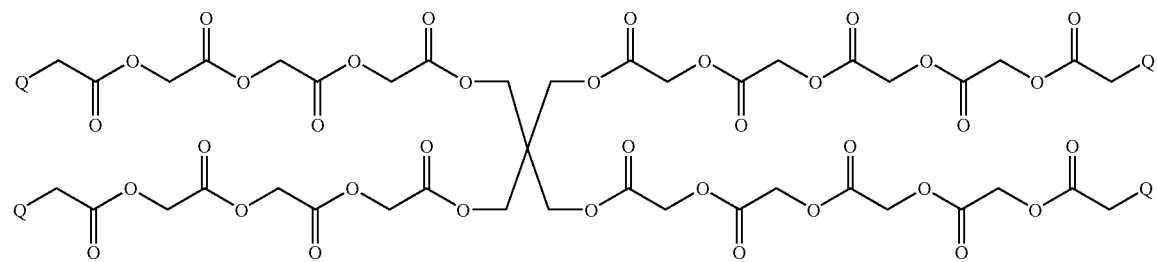
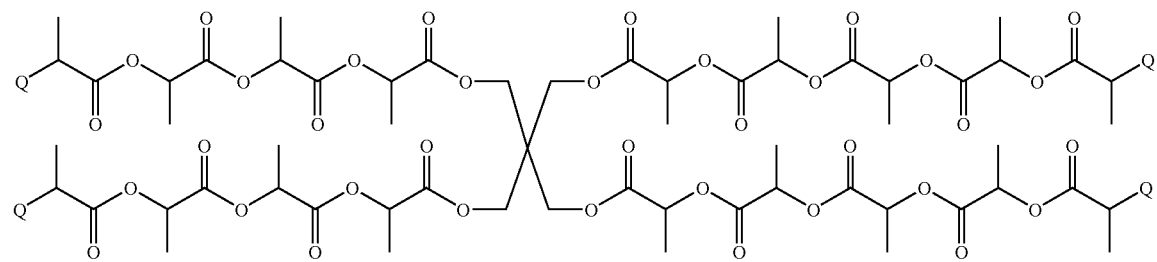
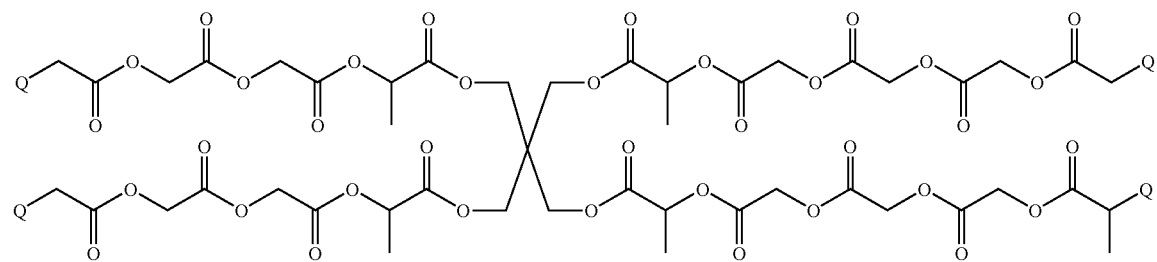
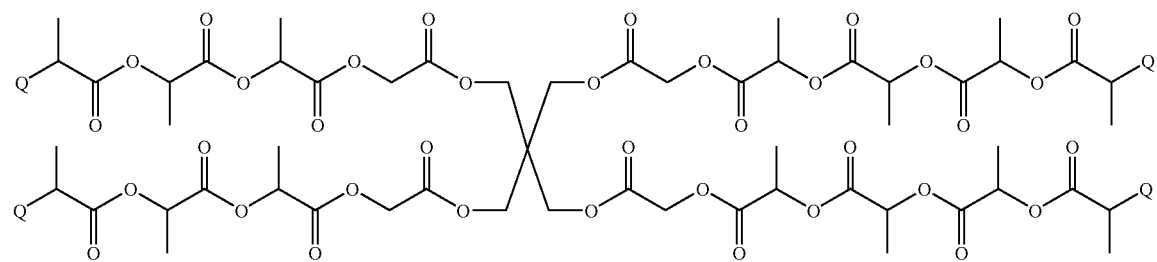

wherein Q is a bond (when part of an oligomer) or F, Cl, Br, or I (when part of a precursor).

For example, the first precursor in the list shown directly above has R as a two carbon diradical, wherein $Y^1$ is —OCH$_2$C(=O)—, b is the integer 2, and w is the integer 2.

Some examples of linear and multi-armed hydrolysable precursors and linkers of the present invention are shown below (e.g., —(Y$^1$)$_b$—O]$_w$R):

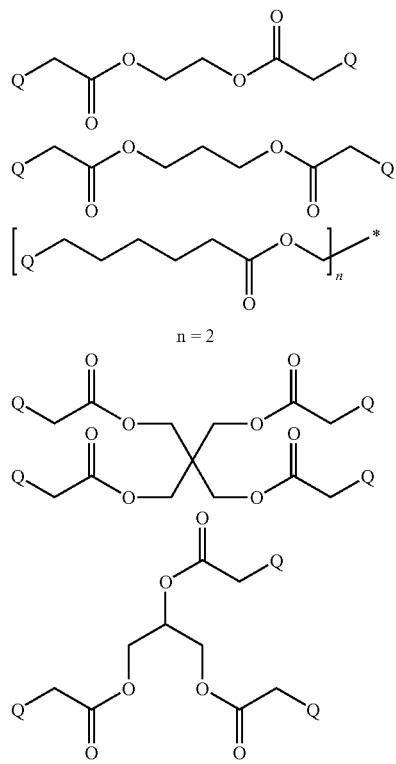

n = 2 wherein Q is a bond (when part of an oligomer) or F, Cl, Br, or I as a replacement for the O atom (when part of a precursor).

For example, the first precursor in the list shown directly above has R as a two carbon diradical, wherein $Y^1$ is —OCH$_2$C(=O)—, b is the integer 2, and w is the integer 2.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

"Aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

The present invention also provides novel therapeutic methods for producing effects or treating diseases by administering to a patient in need thereof a therapeutically effective amount of at least one polymer of the present invention. Examples of effects and diseases include an analgesic effect, cancer, an anti-inflammatory effect, an anti-bacterial effect, an anti-fungal effect, an immunosuppressive effect, an anti-thrombotic effect, psoriasis, inflammatory bowel disease, skin cancer, brain tumor, an anti-infective effect, and pain.

The rate of hydrolysis of Biologically Active Compounds of formula B and D as shown in Scheme 1 and Scheme 2 respectively will depend upon a number of factors, including the functionalization species used and the number of repeat units of functionalization species present on the functionalized Biologically Active Compound (e.g., 1-6). Glycolic acid modified Biologically Active Compound should hydrolyze faster than dioxanone modifies ones, where as lactic acid and caprolactone modified Biologically Active Compound should take much longer to hydrolyze than glycolic acid and dioxanone modified Biologically Active Compound. Furthermore, it is expected that the rate of hydrolysis will increase with the increase in the value of a and b. Thus, the desired time range may be obtained by altering the number of repeat units and type of functionalization species used to functionalize the Biologically Active Compound.

The definitions and examples provided in this application are not intended to be limiting, unless specifically stated.

The starting material for the compounds of the present invention may be a phenolic compound or may be a precursor of a phenolic, such as a methoxyphenol, benzyloxyphenol or acetoxyphenol.

The present invention also provides a blend comprising one or more of the functionalization species with one or more species of phenolic compounds.

The compositions of the present invention may be suitable for administration via a route selected from oral, enteral, parenteral, topical, transdermal, ocular, vitreal, rectal, nasal, pulmonary, and vaginal.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

One aspect of the present invention combines the phenolic compound with one or more of the selected group of compounds to form a functionalized phenolic compound with uses in medicine, as enhanced drugs, drug intermediates, cancer preventing agents, nutrition supplements, nutraceuticals, antioxidants, controlled release preparations, cosmetic applications, flavors, coatings, drug intermediates, solvents for drugs, new monomers for polymerization, and when polymerized, as polymers for biomedical applications, drugs, nutrition supplements, nutraceuticals, drug delivery, cosmetic applications, flavors, and coatings.

The array of functionalized phenolic compounds developed as an aspect of the invention, have a wide range of hydrolysis rates that are controllable. The specific moiety or combination of moieties used for functionalization yields a compound or mixture with specific hydrolysis ranges.

The new functionalized biologically active compounds have more controllable hydrolysis profiles, improved bioavailability, improved efficacy and enhanced functionality. The difunctional compounds polymerize into biodegradable polymers, for example, useful for applications, including biomedical applications, foodstuffs, cosmetics, medicaments, coatings and other uses readily apparent to one skilled in the art.

Bioactive Formulations

In other aspects of the present invention some functionalized biologically active compounds of the present invention are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, where preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, *The Pharmaceutical Basis of Therapeutics*, current edition.

Compounds of the present invention have potent antioxidant activity and increased acidity of their phenolic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

Examples of functionalized biologically active compounds of the present invention are provided for some embodiments of the current invention. It can be extended to other species. This selection is not meant to limit the scope of the invention in any way. Other variations in the procedure may be readily apparent to those skilled in the art.

EXAMPLES

Example 1

Chloro-acetic acid 2-(2-chloro-acetoxy)-ethyl Ester

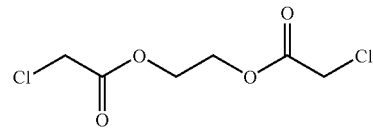

A solution ethylene glycol (100 grams, 1.611 moles), chloroacetic acid (385 grams, 4.031 moles) and paratoluene sulphonic acid (1 gram) in toluene (750 ml) in a 2 lit 4 neck round bottom flask equipped with a mechanical stirrer, Dean-stark apparatus was refluxed for 8 hours, cooled to room temperature. The toluene layer was washed with water (2×300 ml), 5% sodium bicarbonate solution (3×500 ml), water (2×300 ml), dried over sodium sulphate and distilled to get crude 1, which was purified by high vacuum distillation to get pure 1 (242 grams, 69.8%), which slowly crystallized to white crystals m.p: 44° C., $^1$H NMR (CDCl$_3$): δ 4.16 (s, 2H, CH$_2$), 4.85 (s, 2H, CH$_2$).

Example 2

6-Bromo-hexanoic Acid 2-(6-bromo-hexanoyloxy)-ethyl Ester

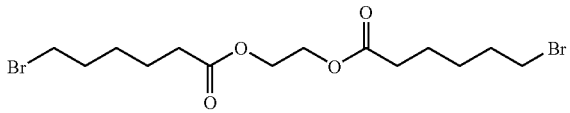

A solution ethylene glycol (5 grams, 80.55 mmoles), 6-bromo hexanoic acid (47 grams, 240.96 mmoles) and paratoluene sulphonic acid (0.5 gram) in toluene (150 ml) in a 500 ml 4 neck round bottom flask equipped with a mechanical stirrer, Dean-stark apparatus was refluxed for 4 hours, cooled to room temperature. The toluene layer was washed with water (2×100 ml), 5% sodium bicarbonate solution (3×50 ml), water (2×100 ml), dried over sodium sulphate and distilled to get example 2 (30 grams, 91%) as a light yellow syrup. m.p: 44° C., $^1$H NMR (CDCl$_3$): δ 1.45 (m, 2H, CH$_2$), 1.59 (m, 2H, CH$_2$), 1.82 (m, 2H, CH$_2$), 2.26 (t, 2H, CH$_2$), 3.34 (t, 2H, CH$_2$), 4.18 (s, 2H, CH$_2$).

Example 3

Chloro-acetic Acid 3-(2-chloro-acetoxy)-2,2-bis-(2-chloro-acetoxymethyl)-propyl Ester

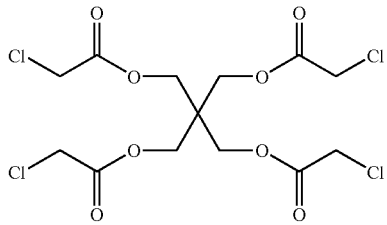

A solution pentaerythritol (25 grams, 183.62 mmoles), chloroacetic acid (105.2 grams, 1.10 moles) and paratoluene sulphonic acid (2 gram) in toluene (500 ml) in a 2 lit 4 neck round bottom flask equipped with a mechanical stirrer, Dean-stark apparatus was refluxed for 8 hours, cooled to room temperature. The toluene layer was washed with water (2×300 ml), 5% sodium bicarbonate solution (3×500 ml), water (2×300 ml), dried over sodium sulphate and distilled to get crude 3, which was purified by recrystallisation from chloroform:Hexane (1:7) to get pure 3 (77 grams, 94.8%), as a white powder. m.p: 94-96° C., $^1$H NMR (CDCl$_3$): δ4.16 (s, 2H, CH$_2$), 4.28 (s, 2H, CH$_2$).

Example 4

Chloro-acetic Acid 2,2-bis-(2-chloro-acetoxymethyl)-butyl Ester

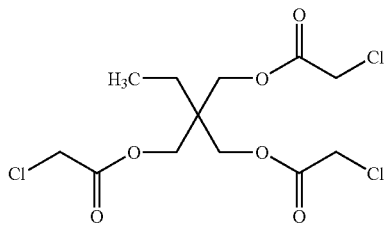

A solution Trimethylolpropane (100 grams, 745.82 mmoles), chloro acetic acid (422 grams, 4.465 moles) and Para toluene sulphonic acid (5 grams) in Toluene (500 ml) in a 2 liter 4 neck round bottom flask equipped with a mechanical stirrer, Dean-stark apparatus was refluxed for 8 hours, cooled to room temperature. The toluene layer was washed with water (2×300 ml), 5% sodium bicarbonate solution (3×500 ml), water (2×300 ml), dried over sodium sulphate and distilled to get the linker as light yellow syrup.

IH NMR (CDCl3) δ 0.9 (t, 3H, CH3), 1.6 (q, 2H, CH2), 4.07 (s, 6H, CH2×3), 4.15 (s, 6H, CH2×3)

Example 5

Aspirin Dimer

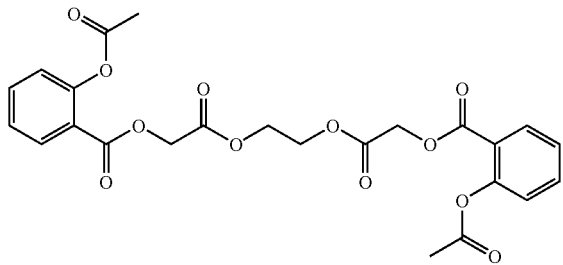

To a solution of Aspirin (25.13 grams, 139.49 mmoles), triethylamine (23.52 grams, 232.43 mmoles) in dry acetone (100 ml) was added chloro-acetic acid 2-(2-chloro-acetoxy)-ethyl ester 1 (10 grams, 46.50 mmoles) and stirred at room temperature for 20 hours. The solid triethylamine hydrochloride is filtered and to the filtrate, cold water (300 ml) was added. The precipitated polymer 5 was filtered, dried and recrystallised from chloroform:hexane (1:6) to get pure dimer 5 (16 grams, 68.4%) as white powder. m.p: 91-92.5° C., $^1$HNMR (CDCl$_3$): δ 2.30 (s, 3H, OAc), 4.40 (s, 2H, CH$_2$), 4.76 (s, 2H, CH$_2$), 7.10 (d, 1H, Ar), 7.32 (t, 1H, Ar), 7.58 (t, 1H, Ar), 8.10 (d, 1H, Ar).

Example 6

Aspirin Tetramer

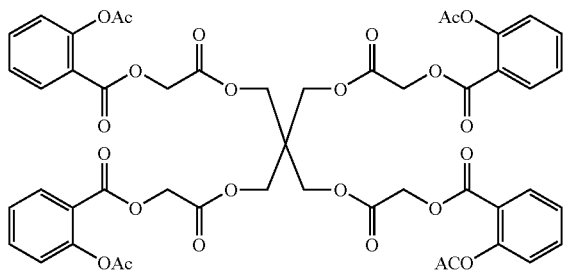

To a solution of Aspirin (20.37 grams, 113.07 mmoles), triethylamine (18.29 grams, 180.74 mmoles) in dry acetone (100 ml) was added tetra chloro linker (10 grams, 22.62 mmoles), example 3 and stirred at room temperature for 20 hours. The solid triethylamine hydrochloride is filtered, acetone distilled off. Crude mass was dissolved in ethyl acetate, washed with 5% sodium bicarbonate solution, dried over sodium sulphate and distilled. The crude 6 was recrystallised from chloroform:hexane (1:6) to get pure 6 (10 grams, 44%) as white powder. m.p: 85-88° C., $^1$HNMR (CDCl$_3$): δ 2.31 (s, 3H, OAc), 4.16 (s, 2H, CH$_2$), 4.78 (s, 2H, CH2), 7.12 (d, 1H, Ar), 7.32 (t, 1H, Ar), 7.60 (t, 1H, Ar), 8.08 (d, 1H, Ar).

Example 7

Aspirin Trimer

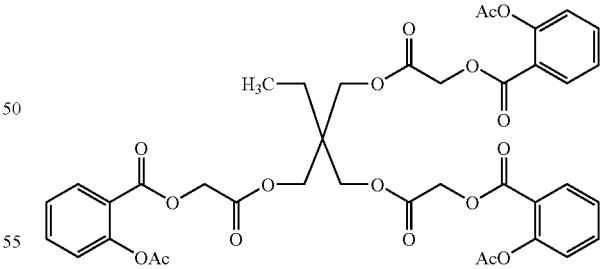

To a solution of Aspirin (124.5 grams, 91.09 mmoles), triethylamine (111.8 grams, 1.104 moles) in dry acetone (500 ml) at reflux temperature was added a solution of Tri chloro linker (50 grams, 137.89 mmoles), example 4, in acetone (100 ml) drop wise. Later further refluxed for 16 hours, cooled to room temperature, the solid triethylamine hydrochloride is filtered, acetone distilled off. Crude mass was dissolved in ethyl acetate, washed with 5% sodium bicarbonate solution, dried over sodium sulphate and distilled. The crude 7 was purified by column chromatography on silica gel using chloroform as eluant to get pure 7 (25 grams, 23.2%) as light yellow syrup: m.p: 85-88° C., $^1$HNMR (CDCl$_3$): δ 0.82 (t, 3H, CH$_3$), 1.38 (q, 2H, CH$_2$), 2.32 (s, 9H, OAc), 4.10 (s, 6H, CH$_2$), 4.80 (s, 6H, CH$_2$), 7.14 (d, 3H, Ar), 7.34 (t, 3H, Ar), 7.60 (t, 3H, Ar), 8.10 (d, 3H, Ar).

Example 8

Naproxen Dimer

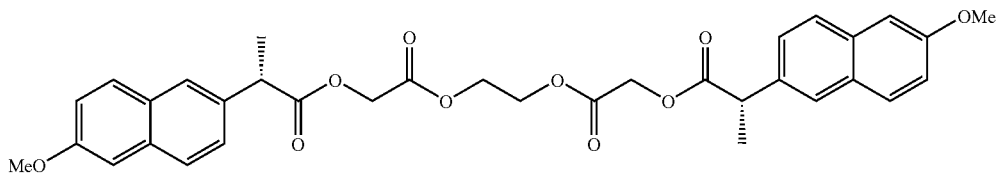

To a solution of Naproxen (56 grams, 243.20 mmoles), triethylamine (36.3 grams, 358.73 mmoles) in dry acetone (150 ml) was added dichloro linker (15 grams, 69.75 mmoles), example 1 and stirred at room temperature for 20 hours. The solid triethylamine hydrochloride is filtered, acetone distilled off. Crude mass was dissolved in ethyl acetate, washed with 5% sodium bicarbonate solution, dried over sodium sulphate and distilled. The crude 8 was purified by column chromatography on silica gel using benzene as eluant to get pure 8 (32 grams, 76.1%) as white powder. m.p: 69-71° C., $^1$HNMR (CDCl$_3$): δ 1.61 (d, 6H, CH$_3$), 3.90 (s, 6H, OCH3), 3.97 (q, 2H, CH), 4.26 (s, 4H, CH2), 4.58 (q, 4H, CH$_2$), 7.10 (m, 4H, Ar), 7.41 (d, 2H, Ar), 7.70 (m, 6H, Ar).

Example 9

Naproxen Tetramer

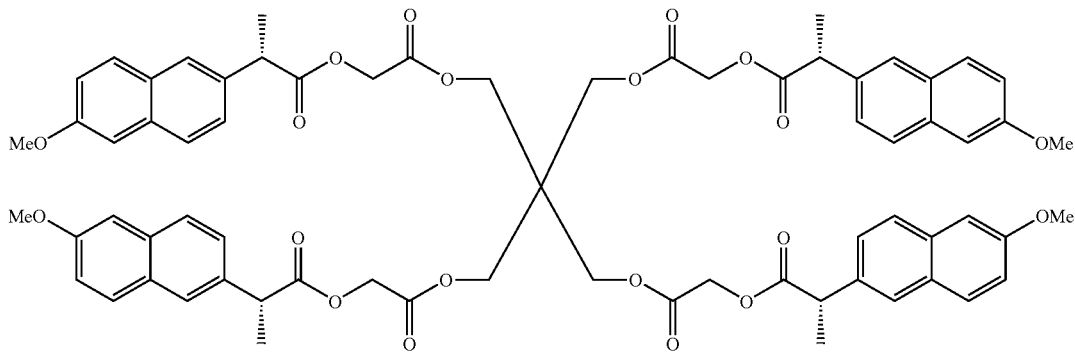

To a solution of Naproxen (13 grams, 56.45 mmoles), triethylamine (9.14 grams, 90.32 mmoles) in dry acetone (50 ml) was added tetrachlorolinker (5 grams, 11.31 mmoles), example 3 and stirred at room temperature for 20 hours. The solid Triethylamine hydrochloride is filtered, acetone distilled off. Crude mass was dissolved in ethyl acetate, washed with 5% sodium bi carbonate solution, dried over sodium sulphate and distilled. The crude 9 was purified by recrystallisation from chloroform:hexane (1:6) to get pure 9 (3 grams, 21.8%) as white powder. m.p: 128-130° C., $^1$HNMR (CDCl$_3$): δ 1.58 (d, 12H, CH3), 3.84 (m, 8H, CH$_2$), 3.88 (s, 12H, OCH$_3$), 3.94 (q, 4H, CH), 4.52 (q, 8H, CH$_2$), 7.10 (m, 8H, Ar), 7.41 (d, 4H, Ar), 7.70 (m, 12H, Ar).

Example 10

Naproxen Trimer

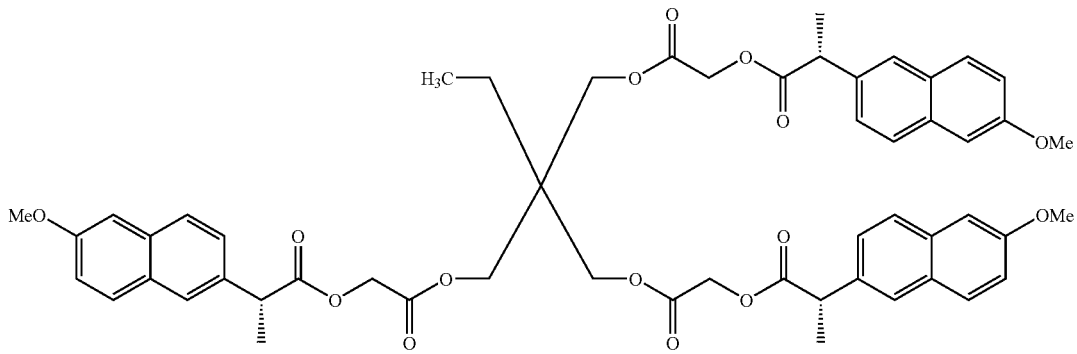

To a solution of Naproxen (127 grams, 551.15 mmoles), triethylamine (83.5 grams, 825.18 mmoles) in dry acetone (500 ml) was added trichloro linker (50 grams, 137.89 mmoles), example 4 and stirred at room temperature for 20 hours. The solid triethylamine hydrochloride is filtered, acetone distilled off. Crude mass was dissolved in ethyl acetate, washed with 5% Sodium bi carbonate solution, dried over sodium sulphate and distilled. The crude 10 was purified by column chromatography on silica gel using benzene as eluant to get pure 10 (30 grams, 23%) as light green thick syrup. $^1$HNMR (CDCl$_3$): δ 0.66 (t, 3H, CH$_3$), 1.15 (q, 2H, CH$_2$), 1.61 (d, 9H, CH$_3$), 3.96 (m, 15H, OCH$_3$, CH$_2$), 4.56 (q, 6H, CH$_2$), 7.08 (m, 6H, Ar), 7.40 (d, 3H, Ar), 7.67 (m, 9H, Ar).

Example 11

Sulindac

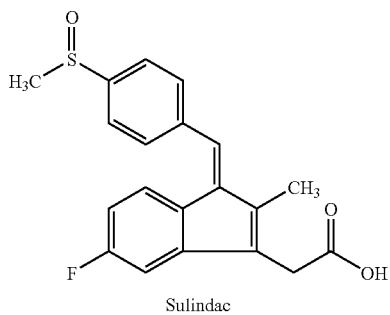

Sulindac

↓

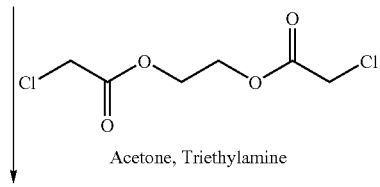

Acetone, Triethylamine

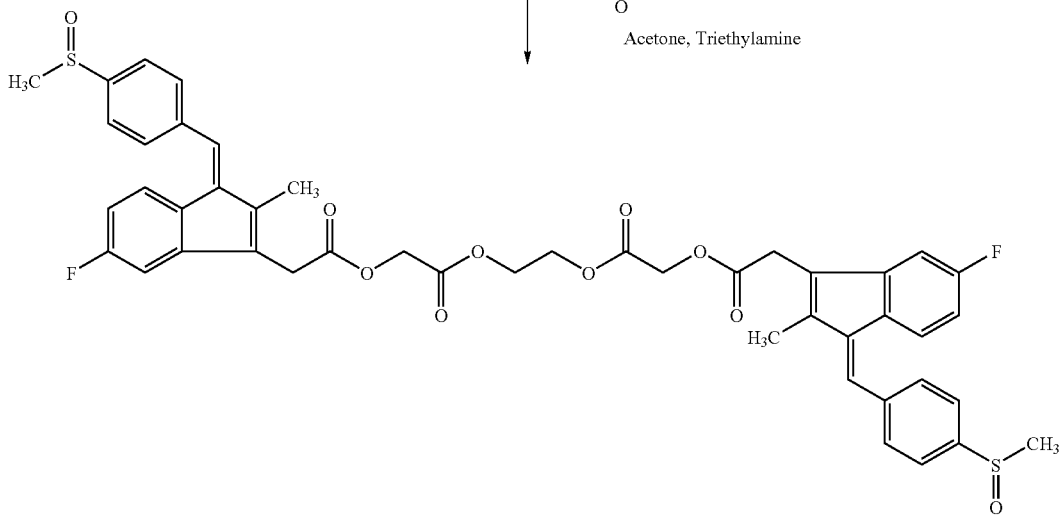

Example 12

Exisulind

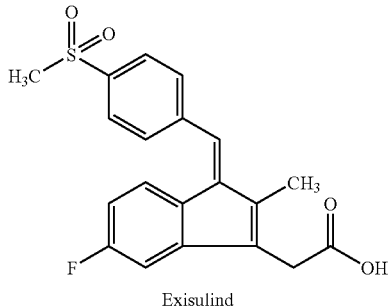

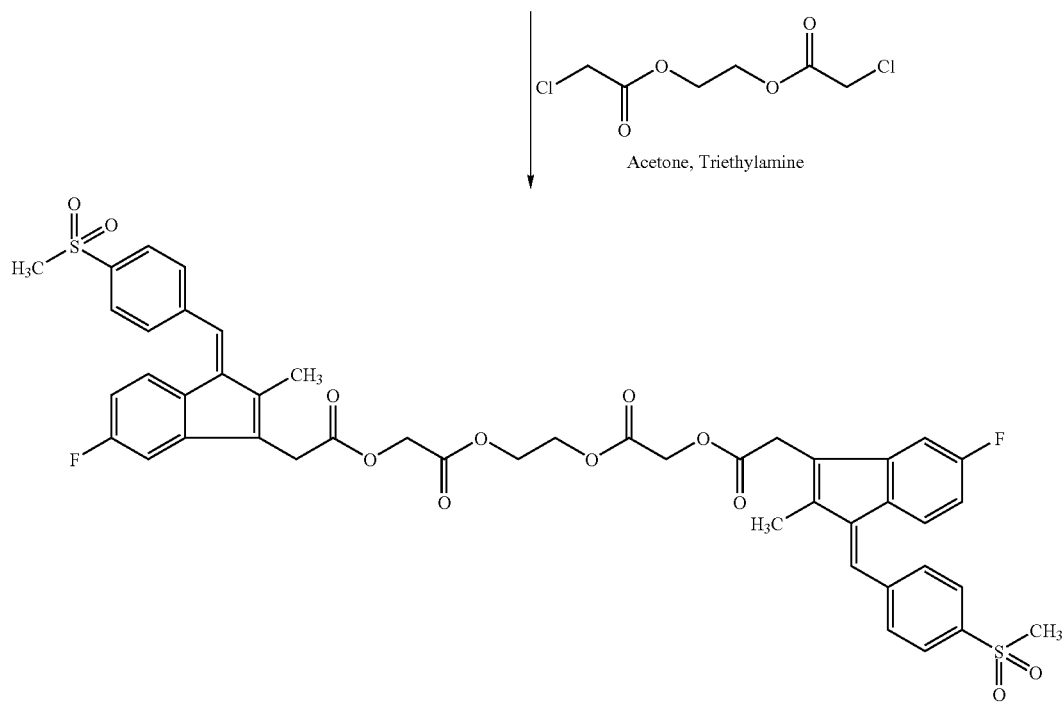

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Embodiment 1

An oligomer or pharmaceutically acceptable salt thereof of formula I or II:

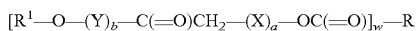

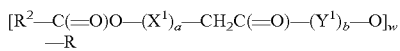

wherein:
$R^1$—O— is a biologically active compound residue;
$R^2$—C(=O)O— is a biologically active compound residue;

X is selected from: —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—.

$X^1$ is selected from: —CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_z$CH$_2$C(=O)O—;

Y is selected from: —C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$—O—(CH$_2$CH$_2$O)$_n$—;

$Y^1$ is selected from: —OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C (=O)— (inverse caprolactone ester moiety), —O(CH$_2$)$_m$C(=O)—, or —O(CH$_2$CH$_2$O)$_n$OCH$_2$C(=O)—;
R is a di-, tri, tetra-, penta- or hexaradical derived from C$_{2-25}$ alkyl, aryl, or aryl-(C$_{1-6}$alkyl)$_{1-3}$-, wherein from 1-3 of the CH$_2$ groups within the alkyl chain are optionally independently replaced by O atoms, such that each of said O atom is attached only to carbon atoms in the alkyl chain, with the proviso that multiple O atoms that replace CH$_2$ groups within the alkyl chain must be separated from each other by at least two carbon atoms and from the di-, tri, tetra-, penta- or hexaradical chain ends by at least one carbon atom; or R is the backbone of a polymer or copolymer bearing carboxylic acid and/or hydroxyl functional groups, where the average molecular weight of the polymer or copolymer is between 500 to 5000 and wherein w is an integer from about 6 to about 50;
each a and b is independently an integer from about 1 to about 10;
each m, n, y, and z is independently an integer from about 2 to about 24; and
w is an integer from about 2 to about 6.

Embodiment 2

An oligomer of Embodiment 1, wherein:
R is a di-, tri, tetra-, penta- or hexaradical derived from C$_{2-12}$alkyl, phenyl, or phenyl-(C$_{1-6}$alkyl)$_{1-3}$-, wherein from 1-3 of the CH$_2$ groups within the alkyl chain are optionally independently replaced by O atoms, such that each of said O atom is attached only to carbon atoms in the alkyl chain, with the proviso that multiple O atoms that replace CH$_2$ groups within the alkyl chain must be separated from each other by at least two carbon atoms and from the di-, tri, tetra-, penta- or hexaradical chain ends by at least one carbon atom;
each a and b is independently an integer from about 1 to about 5; and
w is an integer from about 2 to about 4.

Embodiment 3

An oligomer of Embodiment 1 or 2, wherein:
R—[O]$_w$ is O(CH$_2$)$_2$O, O(CH$_2$)$_3$O, CH(CH$_2$O)$_3$, C(CH$_2$O)$_4$, or C(CH$_2$CH$_3$)(CH$_2$OH)$_3$.

Embodiment 4

An oligomer of Embodiment 1, 2, or 3, wherein:
each X is independently —OC(=O)CH$_2$—, —OC(=O)CH(CH$_3$)—, —OC(=O)CH$_2$OCH$_2$CH$_2$—, or —OC(=O)CH$_2$CH$_2$CH$_2$CH$_2$—.
each X$^1$ is independently —CH$_2$COO—; —CH(CH$_3$)COO—; —CH$_2$CH$_2$OCH$_2$COO—; or —CH$_2$CH$_2$CH$_2$CH$_2$CH$_2$COO—.
each Y is independently —COCH$_2$O—; —COCH(CH$_3$)O—; —COCH$_2$OCH$_2$CH$_2$O—; or —COCH$_2$CH$_2$CH$_2$CH$_2$O—, and
each Y$^1$ is independently —OCH$_2$CO—; —OCH(CH$_3$)CO—; —OCH$_2$CH$_2$OCH$_2$CO—; or —OCH$_2$CH$_2$CH$_2$CH$_2$CH$_2$CO—.

Embodiment 5

An oligomer of Embodiment 1, 2, 3, or 4, wherein:
X is independently —OCOCH$_2$— and —OCOCH(CH$_3$)—;
each X$^1$ is independently —CH$_2$COO— and —CH(CH$_3$)COO—;
each Y is independently —COCH$_2$O— and —COCH(CH$_3$)O—; and,
each Y$^1$ is independently —OCH$_2$CO— and —OCH(CH$_3$)CO—.

Embodiment 6

An oligomer of Embodiment 1, 2, 3, 4, or 5, wherein R$^1$—O— is selected from acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoum-acetate, etilefrine, etiroxate, exalamide, exifone, fendosal, fenoldopam mesilate, fenoterol, fenoxedil, fenticlor, flopropione, floredil, fluorescein, folescutol, formo-terol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochlor-ide, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxo-line, norfenefrine, normolaxol, octopamine, omeprazole, orciprenaline, oxilofrine, oxitriptan, oxyfedrine, oxypertine, oxyphenbutazone, oxyphenisatin acetate, oxyquin-oline, papaverine, paracetanol, parethoxycaine, phenacaine, phenacetin, phenazocine, phenolphthalein, phenprocoumon, phentolamine, phloedrine, picotamide, pimoben-dan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theo-drenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, and xamoterol.

Embodiment 7

An oligomer of Embodiment 1, 2, 3, 4, or 5, wherein R$^1$—O— is:

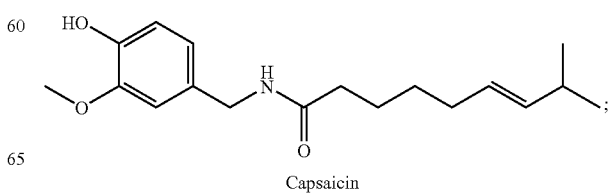

Capsaicin

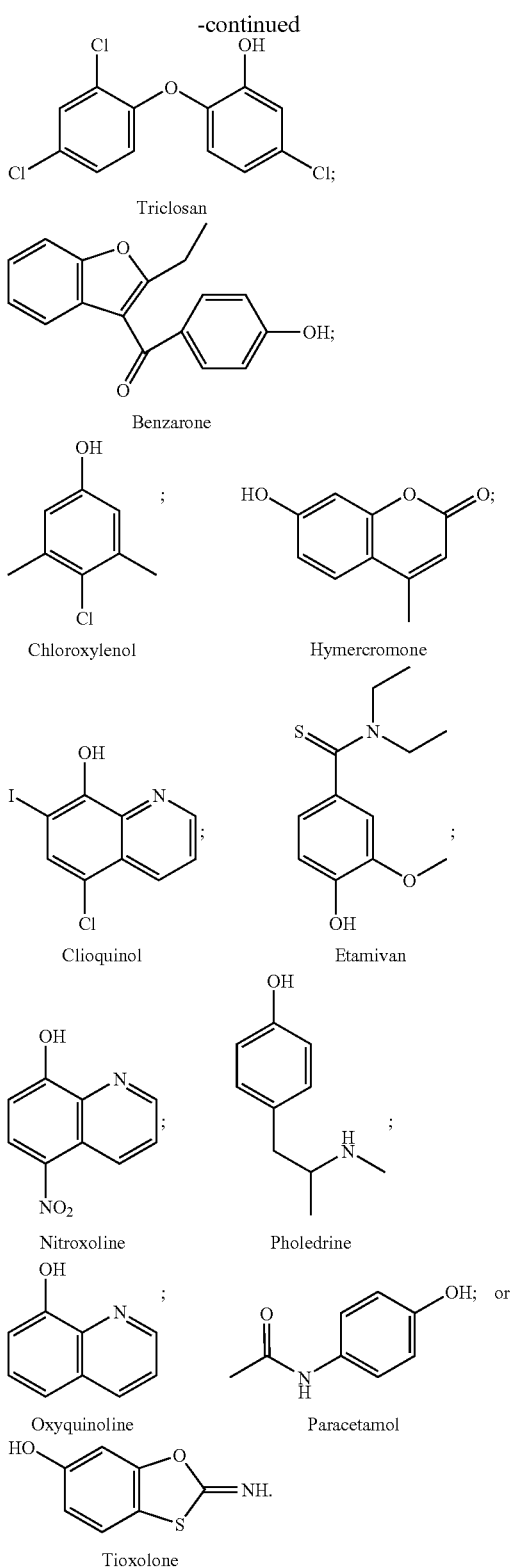

Embodiment 8

An oligomer of Embodiment 1, 2, 3, 4, or 5, wherein $R^2$—C(=O)O— is selected from Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic cid, Mefenamic acid, Naproxen, Nedocromil, Repaglinide, Salazosulfapyridine, Salicylic Acid, Salsalate, and Sarpogrelate.

Embodiment 9

An oligomer of claim Embodiment 1, 2, 3, 4, or 5, wherein $R^2$—C(=O)O— is:

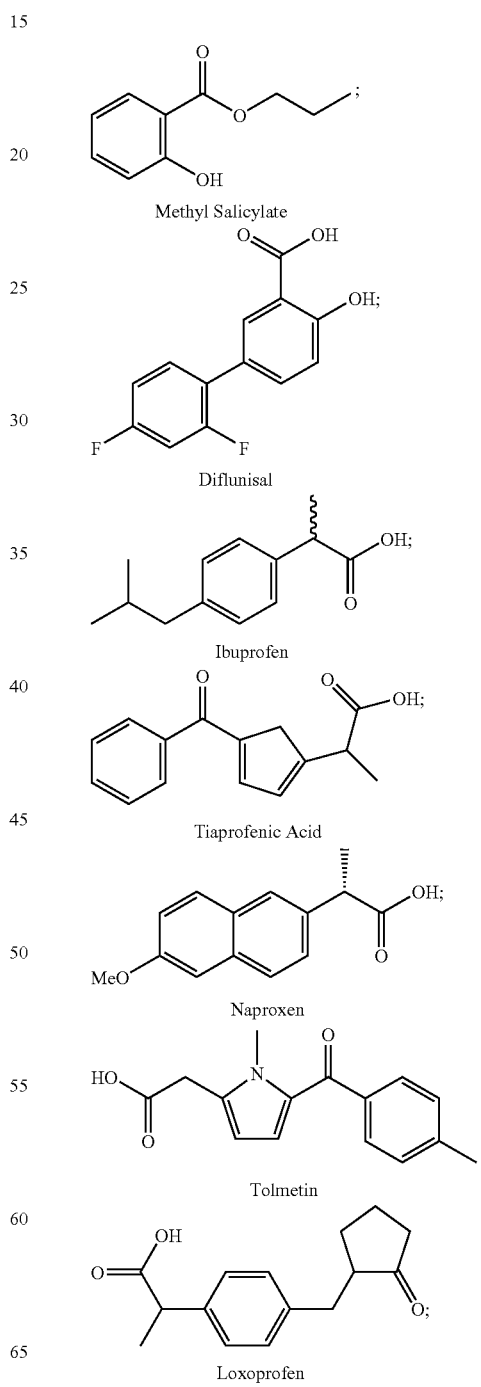

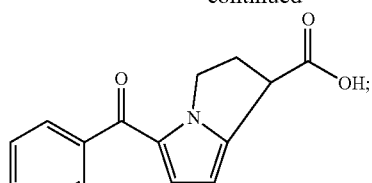

Ketorolac

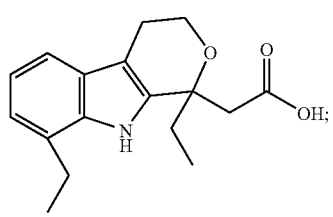

Etodolac

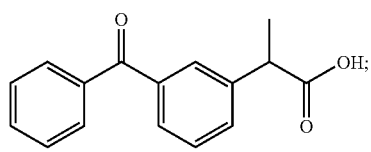

Ketoprofen

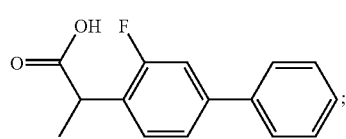

Flurbiprofen

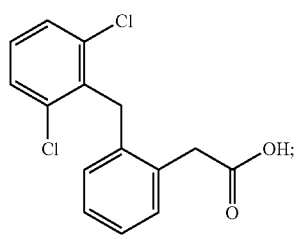

Diclofenac

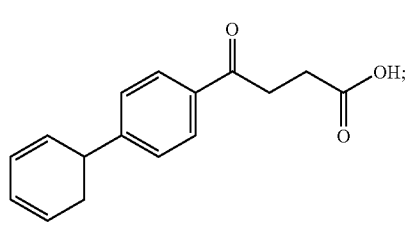

Fenbufen

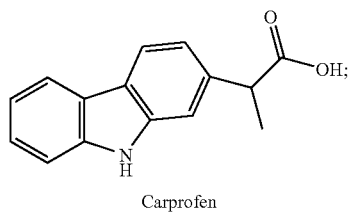

Carprofen

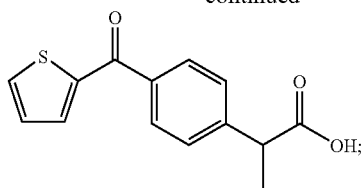

Suprofen

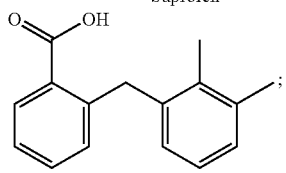

Mefenamic acid

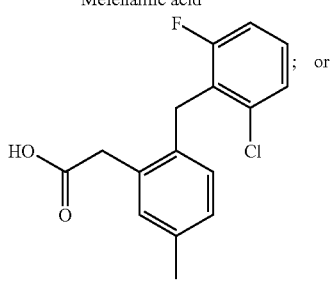

Lumiracoxib

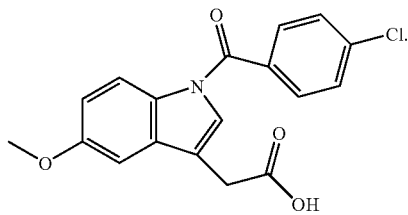

Indometacin

Embodiment 10

An oligomer of Embodiment 1, 2, 3, 4, 5, 6, or 7, wherein $R^1$—O— is selected from capsaicin, coumarins, furanocoumarins, alkaloids, catechins, chromones, chalcones, flavonoids or bioflavonoids, isoflavones, resveratrol, and sinapic acid.

Embodiment 11

An oligomer of Embodiment 1, 2, 3, 4, 5, 6, or 7, wherein $R^1$—O— is selected from 4-hydroxycinnamic acid, caffeic acid, chlorogenic acid, ferulic acid, capsaicin, 4-hydroxycoumarin, psoralen, bergapten, bergaptol, xanthotoxin, isopimpinellin.

Embodiment 12

An oligomer of Embodiment 1, 2, 3, 4, 5, 6, 7, 10, or 11, wherein —OC(=O)]$_w$—R is:

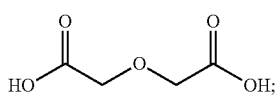

37
-continued

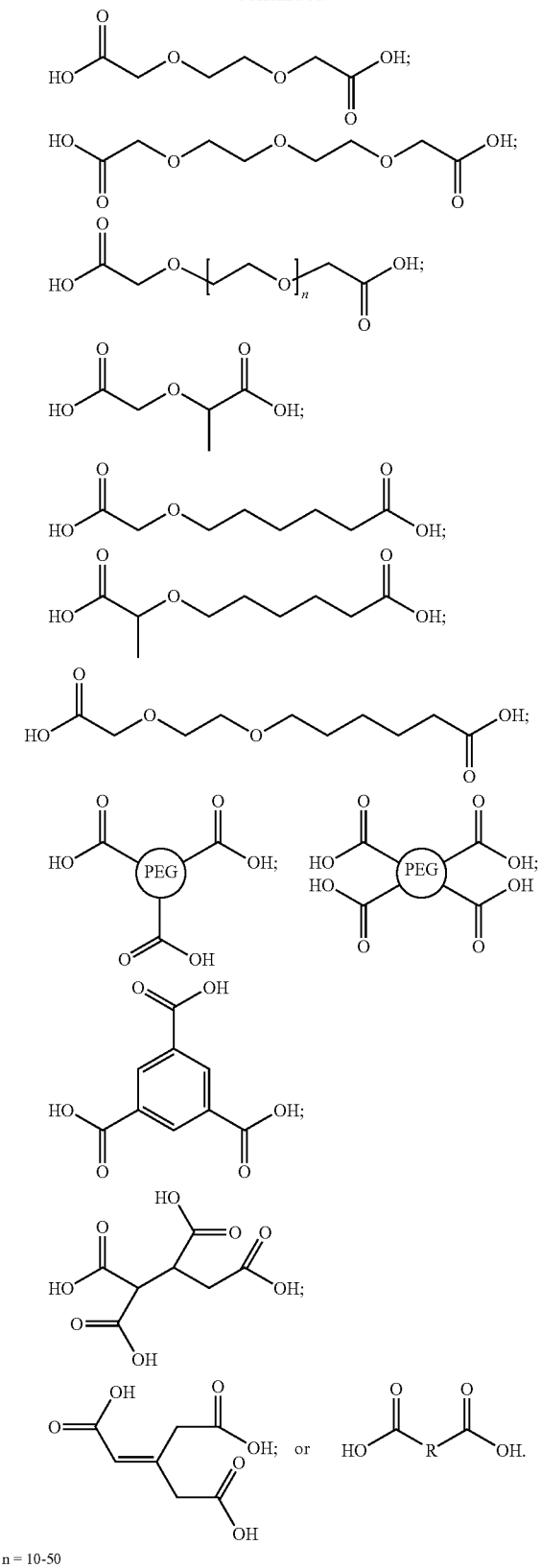

wherein each carboxylic acid proton (H) present in the di- or poly-acid shown is absent in the moiety —OC(=O)]$_w$—R.

38

Embodiment 13

An oligomer of Embodiment 1, 2, 3, 4, 5, 8, or 9, wherein —(Y$^1$)$_b$—O]$_w$R is:

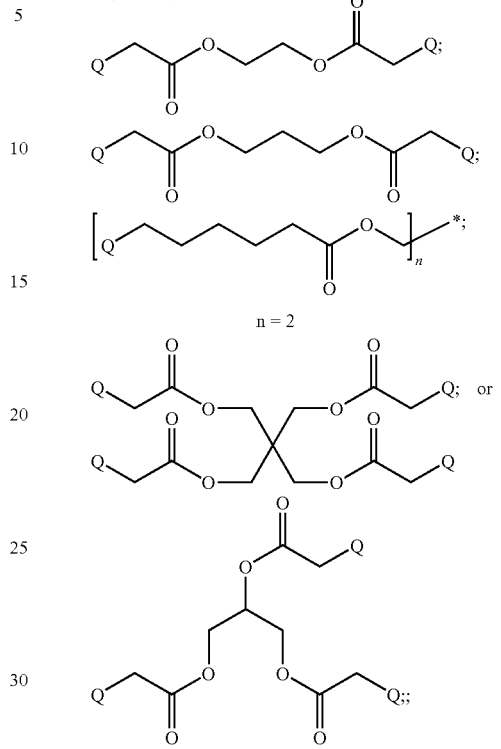

wherein each Q is a bond.

Embodiment 14

An oligomer of Embodiment 1, 2, 3, 4, 5, 6, 7, 10, 11, or 12, wherein —(X)$_a$—OC(=O)]$_w$—R is:

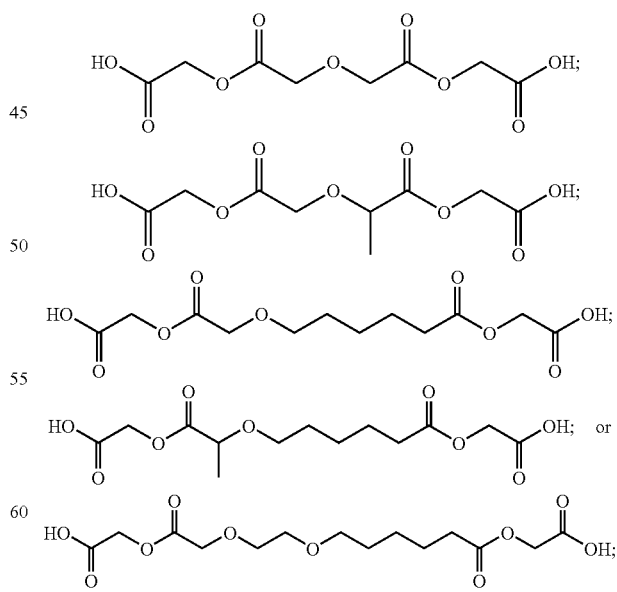

wherein each carboxylic acid proton (H) present in the di-acid shown is absent in the moiety. —(X)$_a$—OC(=O)]$_w$—R.

Embodiment 15

An oligomer of Embodiment 1, 2, 3, 4, 5, 8, 9, or 13, wherein —CH$_2$C(=O)—(Y$^1$)$_b$—O]$_w$R) is:

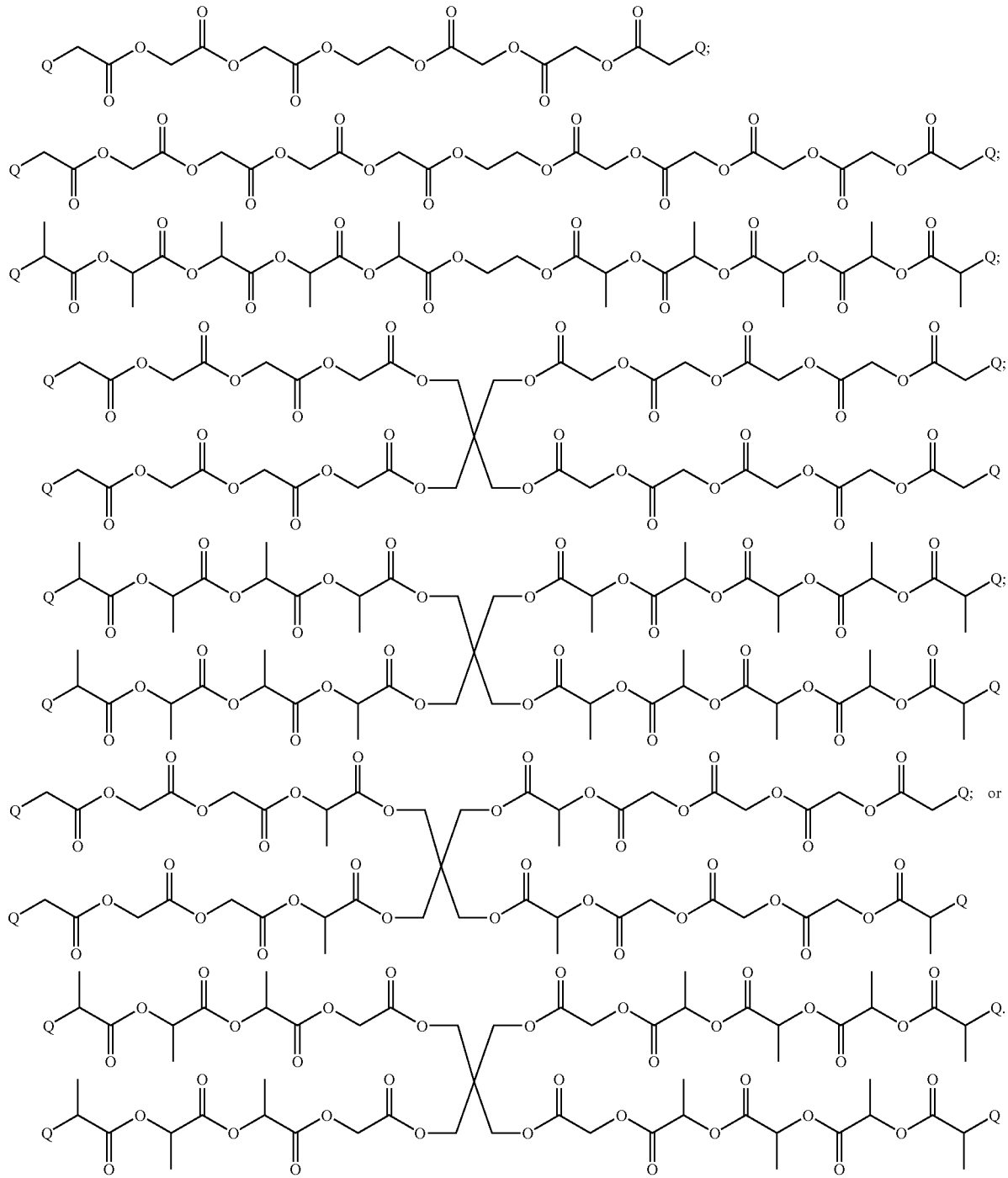

wherein Q is a bond.

Embodiment 16

An oligomer of Embodiment 1, 2, 3, 4, 5, 6, 7, 10, 11, 12, or 14, wherein R$^1$—O— is selected from chalcones, hydroxy-benzoic acid, dihydroxy-benzoic acid, indoles, acetophenones, benzophenones, catechins, flavonoids, coumarins, hydroquinone, naproxen, acetaminophen, and acetylsalicylic acid.

Embodiment 17

A cosmetic composition, comprising at least one compound of Embodiment 1, 2, 3, 4, 5, 6, 7, 8, 9, 10, 11, 12, 13, 14, 15, or 16, and a cosmetic ingredient.

Embodiment 18

A pharmaceutical composition, comprising at least one compound of Embodiment 1, 2, 3, 4, 5, 6, 7, 8, 9, 10, 11, 12, 13, 14, 15, or 16, and a pharmaceutically acceptable excipient.

Embodiment 19

A pharmaceutical composition of Embodiment 18, wherein the composition is suitable for administration via a route selected from oral, enteral, parenteral, topical, transdermal, ocular, vitreal, rectal, nasal, pulmonary, and vaginal.

Embodiment 20

A pharmaceutical composition of Embodiment 18, wherein the phenolic residue in the compound of formula I was derived from a cancer preventing phenolic.

Embodiment 21

A pharmaceutical composition of Embodiment 20, further comprising: an anti-cancer agent.

Embodiment 22

A pharmaceutical composition of Embodiment 18, wherein the phenolic residue of formula I or II is derived from a phenolic compound with antimicrobial properties.

Embodiment 23

A pharmaceutical composition of Embodiment 22, further comprising: an antimicrobial agent.

Embodiment 24

A pharmaceutical composition of Embodiment 18, wherein the phenolic residue in the compound of formula I was derived from a phenolic with anti-inflammatory properties.

Embodiment 25

A pharmaceutical composition of Embodiment 24, further comprising: anti-inflammatory agent.

Embodiment 26

A pharmaceutical composition of Embodiment 18, wherein the phenolic residue in the compound of formula I was derived from a phenolic with pain-reducing properties.

Embodiment 27

A pharmaceutical composition of Embodiment 26, further comprising: a pain reducing agent.

Embodiment 28

A pharmaceutical composition of Embodiment 18, wherein the phenolic residue in the compound of formula I was derived from a phenolic with antioxidant properties.

Embodiment 29

A pharmaceutical composition of Embodiment 28, further comprising: an antioxidant agent.

Embodiment 30

A suture coating, comprising: at least one oligomer of Embodiment 1, 2, 3, 4, 5, 6, 7, 8, 9, 10, 11, 12, 13, 14, 15, or 16.

Embodiment 31

An antimicrobial agent, comprising: at least one oligomer of Embodiment 1, 2, 3, 4, 5, 6, 7, 8, 9, 10, 11, 12, 13, 14, 15, or 16.

Embodiment 32

A therapeutic method for treating a disease in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 33

A therapeutic method for producing an analgesic effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 34

A therapeutic method for treating cancer in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 35

A therapeutic method for producing an anti-inflammatory effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 36

A therapeutic method for producing an anti-bacterial effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 37

A therapeutic method for producing an anti-fungal effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 38

A therapeutic method for producing an immunosuppressive effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 39

A therapeutic method for producing an anti-thrombotic effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 40

A therapeutic method for treating psoriasis, inflammatory bowel disease, skin cancer, or a brain tumor in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 41

A therapeutic method for producing an anti-infective effect in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

Embodiment 42

A therapeutic method for treating pain in a patient, comprising: administering to a patient in need of such therapy, an effective amount of at least one oligomer of Embodiment 1, 2, 3, 4, 5, 6, 7, 8, 9, 10, 11, 12, 13, 14, 15, or 16.

What is claimed is:

1. An oligomer or pharmaceutically acceptable salt thereof of formula I or II:

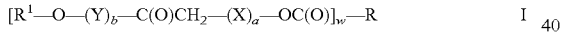

$$[R^1—O—(Y)_b—C(O)CH_2—(X)_a—OC(O)]_w—R \quad\quad I$$

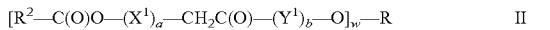

$$[R^2—C(O)O—(X^1)_a—CH_2C(O)—(Y^1)_b—O]_w—R \quad\quad II$$

wherein:

$R^1$—O— is a biologically active compound residue;

$R^2$—C(=O)O— is a biologically active compound residue;

X is selected from: —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;

$X^1$ is selected from: —CH$_2$C(=O)O— (glycolic acid moiety), —CH(CH$_3$)C(=O)O— (lactic acid moiety), —CH$_2$CH$_2$OCH$_2$C(=O)O— (dioxanone acid moiety), —CH$_2$CH$_2$CH$_2$CH$_2$CH$_2$C(=O)O— (caprolactone acid moiety), —(CH$_2$)$_y$C(=O)O—, or —(CH$_2$CH$_2$O)$_n$CH$_2$C(=O)O—;

Y is selected from: —C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$—O—(CH$_2$CH$_2$O)$_n$—;

$Y^1$ is selected from: —OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

R is a di-, tri, tetra-, penta- or hexaradical derived from $C_{2-25}$ alkyl, aryl, or aryl-($C_{1-6}$alkyl)$_{1-3}$-, wherein from 1-3 of the CH$_2$ groups within the alkyl chain are optionally independently replaced by O atoms, such that each of said O atom is attached only to carbon atoms in the alkyl chain, with the proviso that multiple O atoms that replace CH$_2$ groups within the alkyl chain must be separated from each other by at least two carbon atoms and from the di-, tri, tetra-, penta- or hexaradical chain ends by at least one carbon atom; or R is the backbone of a polymer or copolymer bearing carboxylic acid and/or hydroxyl functional groups, where the average molecular weight of the polymer or copolymer is between 500 to 5000 and wherein w is an integer from about 6 to about 50;

each a and b is independently an integer from about 1 to about 10;

each m, n, y, and z is independently an integer from about 2 to about 24; and w is an integer from about 2 to about 6.

2. An oligomer of claim 1, wherein:

R is a di-, tri, tetra-, penta- or hexaradical derived from $C_{2-12}$alkyl, phenyl, or phenyl-($C_{1-6}$alkyl)$_{1-3}$-, wherein from 1-3 of the CH$_2$ groups within the alkyl chain are optionally independently replaced by O atoms, such that each of said O atom is attached only to carbon atoms in the alkyl chain, with the proviso that multiple O atoms that replace CH$_2$ groups within the alkyl chain must be separated from each other by at least two carbon atoms and from the di-, tri, tetra-, penta- or hexaradical chain ends by at least one carbon atom;

each a and b is independently an integer from about 1 to about 5; and w is an integer from about 2 to about 4.

3. An oligomer of claim 1, wherein:

R—[O]$_w$ is O(CH$_2$)$_2$O, O(CH$_2$)$_3$O, CH(CH$_2$O)$_3$, C(CH$_2$O)$_4$, or C(CH$_2$CH$_3$)(CH$_2$OH)$_3$.

4. An oligomer of claim 1, wherein:

each X is independently —OC(=O)CH$_2$—, —OC(=O)CH(CH$_3$)—, —OC(=O)CH$_2$OCH$_2$CH$_2$—, or —OC(=O)CH$_2$CH$_2$CH$_2$CH$_2$CH$_2$—;

each $X^1$ is independently —CH$_2$COO—; —CH(CH$_3$)COO—; —CH$_2$CH$_2$OCH$_2$COO—; or —CH$_2$CH$_2$CH$_2$CH$_2$CH$_2$COO—;

each Y is independently —COCH$_2$O—; —COCH(CH$_3$)O—; —COCH$_2$OCH$_2$CH$_2$O—; or —COCH$_2$CH$_2$CH$_2$CH$_2$CH$_2$O—; and each $Y^1$ is independently —OCH$_2$CO—; —OCH(CH$_3$)CO—; —OCH$_2$CH$_2$OCH$_2$CO—; or —OCH$_2$CH$_2$CH$_2$CH$_2$CH$_2$CO—.

5. An oligomer of claim 4, wherein:

X is independently —OCOCH$_2$— and —OCOCH(CH$_3$)—;

each $X^1$ is independently —CH$_2$COO— and —CH(CH$_3$)COO—;

each Y is independently —COCH$_2$O— and —COCH(CH$_3$)O—; and, each $Y^1$ is independently —OCH$_2$CO— and —OCH(CH$_3$)CO—.

6. An oligomer of claim 1 wherein $R^1$—O— is selected from acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, buphcniodc, capsaicin, chlorotrimliscnc, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethyistiibestroi, diflunisal, diiodohydroxyquinoiine, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoum-acetate, etilefrine, etiroxate, exalamide, exifone, fendosal, fenodolpham mesilate, fenoterol, fenoxedil, fenticlor, flopropione, floredil, fluorescein, folescutol, formo-terol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipritlavone, isoetarine, isoprenaline, isoxsuprine, itopride hydrochioride, ketobemidone, khellin, labetalol, lactyiphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetamol, parethoxycaine, phenacaine, phenacetin, phenazocine, phenolphthalein, phenprocoumon, phentolamine, pholedrine, picotamide, pimoben-dan, prenalterol, primaquine, progabide, propanidid, protokylol, proxymetacaine, raloxifene hydrochloride; repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theo-drenaline, tioclomarol, tioxolone, a-tocopherol (vitamin E), tofisopam, tolcapone, tolterodine, tranilast, tretoquinol, triclosan, trimazosin, trimetazidine, trimethobenz-amide, trimethoprim, trimetozine, trimetrexate glucuronate, troxipide, verapamil, vesnarinone, vetrabutine, viloxazine, warfarin, and xamoterol.

7. An oligomer of claim 6, wherein $R^1$—O— is selected from benzarone, chloroxylenol, clioquinol, etamivan, hymecromone, nitroxoline, oxyquinoline, paracetamol, pholedrine, tioxolone, and tricolsan.

8. An oligomer of claim 1, wherein $R^2$—C(=O)O— is selected from Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic cid, Mefenamic acid, Naproxen, Nedocromil, Repaglinide, Salazosulfapyridine, Salicylic Acid, Salsalate, and Sarpogrelate.

9. An oligomer of claim 1, wherein $R^2$—C(=O)O— is selected from methyl salicylate, diflusinal, ibuprofen, tiaprofenic acid, naproxen, tolmetin, losoprofen, ketorolac, etodolac, ketoprofen, fluribprofen, diclofenac, fenbufen, carprofen, suprofen, mefenamic acid, lumiracoxib, and indomethacin.

10. An oligomer of claim 1, wherein $R^1$—O— is selected from capsaicin, coumarins, furanocoumarins, alkaloids, catechins, chromones, chalcones, flavonoids or bioflavonoids, isoflavones, resveratrol, and sinapic acid.

11. An oligomer of claim 1, wherein $R^1$—O— is selected from 4-hydroxycinnamic acid, caffeic acid, chlorogenic acid, ferulic acid, capsaicin, 4-hydroxycoumarin, psoralen, bergapten, bergaptol, xanthotoxin, isopimpinellin.

12. An oligomer of claim 1, wherein —OC(=O)]$_w$—R is:

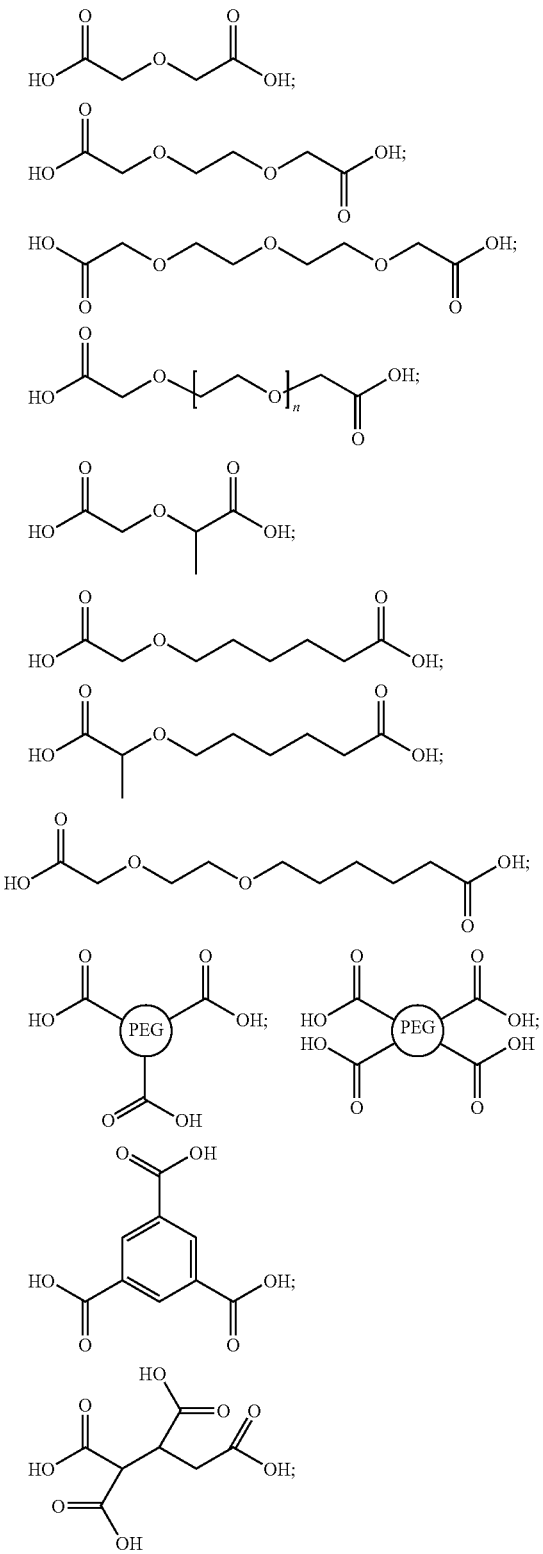

-continued

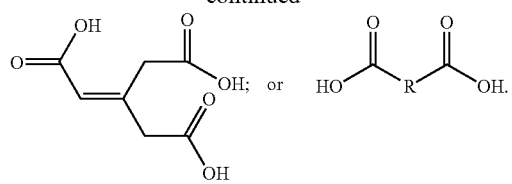

n = 10-50 wherein each carboxylic acid proton (H) present in the di- or poly-acid shown is absent in the moiety —OC(=O)]$_w$—R.

13. An oligomer of claim 1, wherein —(Y$^1$)$_b$—O]$_w$R is:

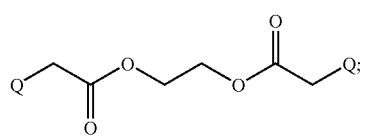

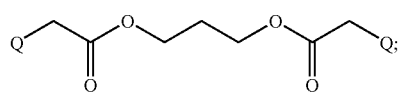

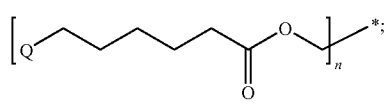

n = 2

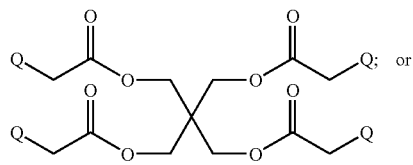 or

-continued

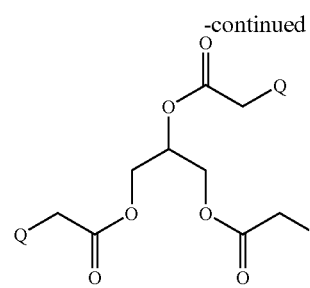

wherein each Q is a bond.

14. An oligomer of claim 1, wherein —(X)$_a$—OC(=O)]$_w$—R is:

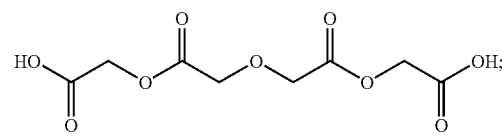

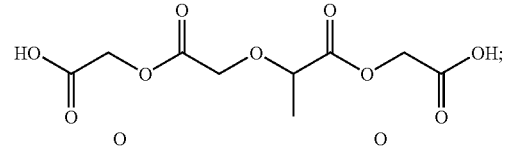

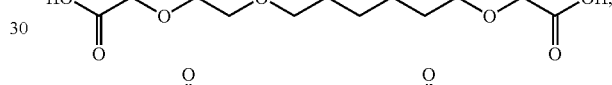

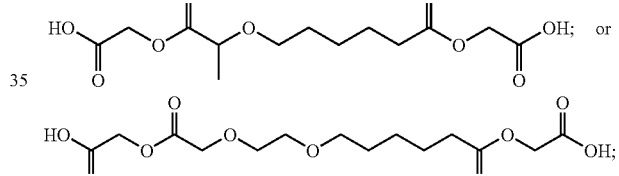 or

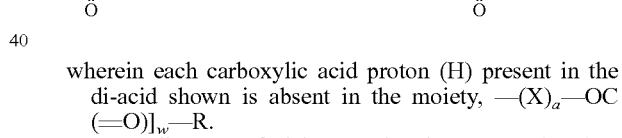

wherein each carboxylic acid proton (H) present in the di-acid shown is absent in the moiety, —(X)$_a$—OC(=O)]$_w$—R.

15. An oligomer of claim 1, wherein —CH$_2$C(=O)—(Y$^1$)$_b$—O]$_w$R) is:

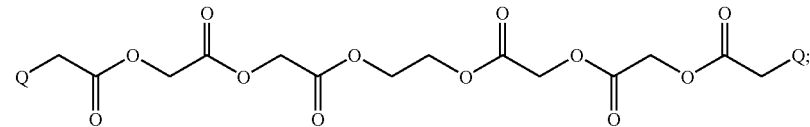

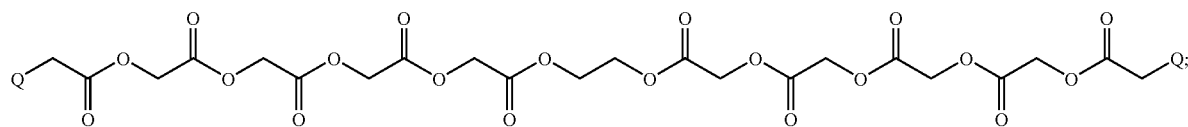

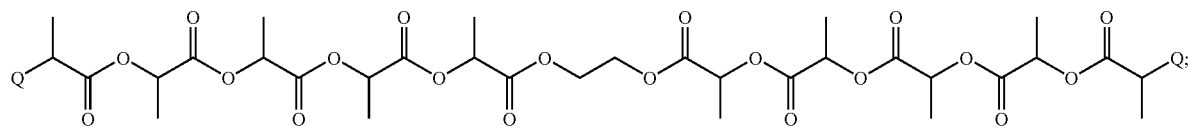

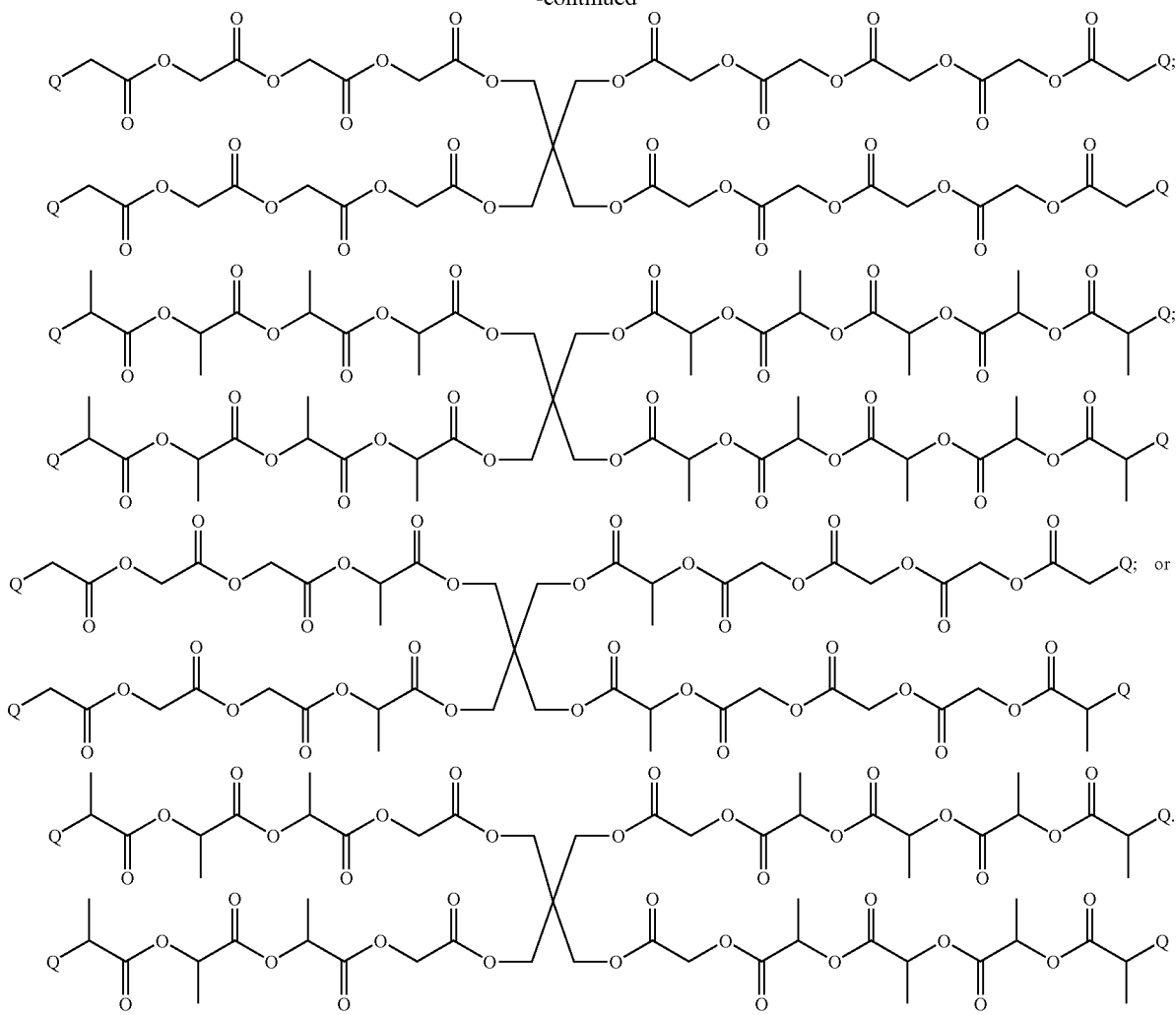

wherein Q is a bond.

16. An oligomer of claim 1, wherein $R^1$—O— is selected from chalcones, hydroxy-benzoic acid, dihydroxy-benzoic acid, indoles, acetophenones, benzophenones, catechins, flavonoids, coumarins, hydroquinone, naproxen, acetaminophen, and acetylsalicylic acid.

17. A cosmetic composition, comprising at least one compound of claim 1 and a cosmetic ingredient.

18. A pharmaceutical composition, comprising at least one compound of claim 1 and a pharmaceutically acceptable excipient.

19. A pharmaceutical composition of claim 18, wherein the composition is suitable for administration via a route selected from oral, enteral, parenteral, topical, transdermal, ocular, vitreal, rectal, nasal, pulmonary, and vaginal.

20. A pharmaceutical composition of claim 18, wherein the phenolic residue of formula I or II is derived from a phenolic compound with antimicrobial properties.

21. A pharmaceutical composition of claim 20, further comprising: an antimicrobial agent.

22. A pharmaceutical composition of claim 18, wherein the phenolic residue in the compound of formula I was derived from a phenolic with anti-inflammatory properties.

23. A pharmaceutical composition of claim 22, further comprising: anti-inflammatory agent.

24. A pharmaceutical composition of claim 18, wherein the phenolic residue in the compound of formula I was derived from a phenolic with pain-reducing properties.

25. A pharmaceutical composition of claim 24, further comprising: a pain reducing agent.

26. A pharmaceutical composition of claim 18, wherein the phenolic residue in the compound of formula I was derived from a phenolic with antioxidant properties.

27. A pharmaceutical composition of claim 26, further comprising: an antioxidant agent.

28. A suture coating, comprising: at least one oligomer of claim 1.

29. An antimicrobial agent, comprising: at least one oligomer of claim 1, wherein the biologically active compound has an antimicrobial effect.

30. A therapeutic method for treating a disease in a patient, comprising: administering to a patient in need of such therapy, an effective amount of at least one oligomer of claim 1.

31. A therapeutic method for producing an analgesic effect in a patient, comprising: administering to a patient in need of such therapy, an effective amount of at least one oligomer of claim 1, wherein the biologically active compound has an analgesic effect.

32. A therapeutic method for treating cancer in a patient, comprising: administering to a patient in need of such therapy, an effective amount of at least one oligomer of claim 1, wherein the biologically active compound has an anti-cancer effect.

33. A therapeutic method for producing an anti-inflammatory effect in a patient, comprising: administering to a patient in need of such therapy, an effective amount of at least one oligomer of claim 1, wherein the biologically active compound has anti-inflammatory effect.

34. A therapeutic method for producing an anti-bacterial effect in a patient, comprising: administering to a patient in need of such therapy, an effective amount of at least one oligomer of claim 1, wherein the biologically active compound has anti-bacterial effect.

35. A therapeutic method for producing an anti-fungal effect in a patient, comprising: administering to a patient in need of such therapy an effective amount of at least one oligomer of claim 1 wherein the biologically active compound has an anti-fungal effect.

36. A therapeutic method for producing an immunosuppressive effect in a patient, comprising: administering to a patient in need of such therapy, an effective amount of at least one oligomer of claim 1, wherein the biologically active compound has an immunosuppressive effect.

37. A therapeutic method for producing an anti-thrombotic effect in a patient, comprising: administering to a patient in need of such therapy, an effective amount of at least one oligomer of claim 1, wherein the biologically active compound has anti-thrombotic effect.

38. A therapeutic method for treating psoriasis, or inflammatory bowel disease in a patient, comprising: administering to a patient in need of such therapy, an effective mount of at least one oligomer of claim 1, wherein the biologically active compound has an anti-psoriasis or anti-inflammatory bowel disease effect.

* * * * *